US010960210B2

(12) United States Patent
Srivastava et al.

(10) Patent No.: US 10,960,210 B2
(45) Date of Patent: Mar. 30, 2021

(54) METHOD AND APPARATUS FOR PAIN MANAGEMENT WITH SLEEP DETECTION

(71) Applicant: Boston Scientific Neuromodulation Corporation, Valencia, CA (US)

(72) Inventors: Kyle Harish Srivastava, Saint Paul, MN (US); Bryan Allen Clark, Forest Lake, MN (US); Elizabeth Mary Annoni, White Bear Lake, MN (US); Jianwen Gu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 159 days.

(21) Appl. No.: 15/888,808

(22) Filed: Feb. 5, 2018

(65) Prior Publication Data
US 2018/0229040 A1 Aug. 16, 2018

Related U.S. Application Data

(60) Provisional application No. 62/457,456, filed on Feb. 10, 2017.

(51) Int. Cl.
*A61N 1/00* (2006.01)
*A61N 1/36* (2006.01)
(Continued)

(52) U.S. Cl.
CPC ........ *A61N 1/36139* (2013.01); *A61B 5/4812* (2013.01); *A61B 5/4836* (2013.01);
(Continued)

(58) Field of Classification Search
CPC ............ A61N 1/36139; A61N 1/36135; A61N 1/3605; A61N 1/36078; A61N 1/36071;
(Continued)

(56) References Cited

U.S. PATENT DOCUMENTS

| 4,297,685 A | 10/1981 | Brainard, II |
| 5,187,675 A | 2/1993 | Dent et al. |

(Continued)

FOREIGN PATENT DOCUMENTS

| AU | 2017335497 B2 | 4/2020 |
| AU | 2017334841 B2 | 7/2020 |

(Continued)

OTHER PUBLICATIONS

"2015 Sleep in America® Poll Sleep and Pain—Summary of Findings", National Sleep Foundation, (2015), 1-54.
(Continued)

*Primary Examiner* — Scott M. Getzow
(74) *Attorney, Agent, or Firm* — Schwegman Lundberg & Woessner, P.A.

(57) ABSTRACT

An Example of a system for providing a patient with pain management may include a sleep monitoring circuit, a pain relief device, and a control circuit. The sleep monitoring circuit may be configured to sense one or more sleep signals from the patient and to determine a sleep state of the patient using the one or more sleep signals. The one or more sleep signals may include one or more physiological signals corresponding to the sleep state of the patient. The pain relief device may be configured to deliver one or more pain relief therapies. The control circuit may be configured to control the delivery of the one or more pain relief therapies using therapy parameters and to adjust the therapy parameters based on the determined sleep state.

20 Claims, 5 Drawing Sheets

US 10,960,210 B2
Page 2

(51) Int. Cl.
- *A61B 5/00* (2006.01)
- *A61B 5/01* (2006.01)
- *A61B 5/0402* (2006.01)
- *A61B 5/0476* (2006.01)
- *A61B 5/024* (2006.01)
- *A61B 5/11* (2006.01)

(52) U.S. Cl.
CPC ............ *A61N 1/36071* (2013.01); *A61B 5/01* (2013.01); *A61B 5/02416* (2013.01); *A61B 5/0402* (2013.01); *A61B 5/0476* (2013.01); *A61B 5/1118* (2013.01); *A61B 5/4824* (2013.01); *A61N 1/3614* (2017.08); *A61N 1/36021* (2013.01)

(58) Field of Classification Search
CPC .............. A61N 1/3614; A61N 1/36021; A61B 5/4812; A61B 5/4824; A61B 5/02416; A61B 5/0476; A61B 5/0402; A61B 5/01; A61B 5/4836; A61B 5/1118
See application file for complete search history.

(56) References Cited

U.S. PATENT DOCUMENTS

| | | |
|---|---|---|
| 5,774,591 A | 6/1998 | Black et al. |
| 6,016,103 A | 1/2000 | Leavitt |
| 6,076,011 A | 6/2000 | Hoover |
| 6,088,040 A | 7/2000 | Oda et al. |
| 6,173,260 B1 | 1/2001 | Slaney |
| 6,480,734 B1 | 11/2002 | Zhang et al. |
| 6,497,658 B2 | 12/2002 | Roizen et al. |
| 6,654,632 B2 | 11/2003 | Lange et al. |
| 6,659,968 B1 | 12/2003 | McClure |
| 6,731,984 B2 | 5/2004 | Cho et al. |
| 6,871,099 B1 | 3/2005 | Whitehurst et al. |
| 7,001,337 B2 | 2/2006 | Dekker |
| 7,004,907 B2 | 2/2006 | Banet et al. |
| 7,177,686 B1 | 2/2007 | Turcott |
| 7,189,204 B2 | 3/2007 | Ni et al. |
| 7,222,075 B2 | 5/2007 | Petrushin |
| 7,299,086 B2 | 11/2007 | McCabe et al. |
| 7,376,457 B2 | 5/2008 | Ross |
| 7,407,485 B2 | 8/2008 | Huiku |
| 7,463,927 B1 | 12/2008 | Chaouat |
| 7,566,308 B2 | 7/2009 | Stahmann |
| 7,627,475 B2 | 12/2009 | Petrushin |
| 7,636,602 B2 | 12/2009 | Baru Fassio et al. |
| 7,650,184 B2 | 1/2010 | Walter |
| 7,678,061 B2 | 3/2010 | Lee et al. |
| 7,775,993 B2 | 8/2010 | Heruth et al. |
| 7,957,809 B2 | 6/2011 | Bourget et al. |
| 7,986,991 B2 | 7/2011 | Prichep |
| 8,019,439 B2 | 9/2011 | Kuzma et al. |
| 8,055,348 B2 | 11/2011 | Heruth et al. |
| 8,083,682 B2 | 12/2011 | Dalal et al. |
| 8,192,376 B2 | 6/2012 | Lovett et al. |
| 8,209,182 B2 | 6/2012 | Narayanan |
| 8,290,596 B2 | 10/2012 | Wei et al. |
| 8,332,038 B2 | 12/2012 | Heruth et al. |
| 8,398,556 B2 | 3/2013 | Sethi et al. |
| 8,447,401 B2 | 5/2013 | Miesel et al. |
| 8,475,370 B2 | 7/2013 | McCombie et al. |
| 8,529,459 B2 | 9/2013 | Malker et al. |
| 8,606,356 B2 | 12/2013 | Lee et al. |
| 8,688,221 B2 | 4/2014 | Miesel |
| 8,744,587 B2 | 6/2014 | Miesel et al. |
| 8,805,518 B2 | 8/2014 | King et al. |
| 9,066,659 B2 | 6/2015 | Thakur et al. |
| 9,072,870 B2 | 7/2015 | Wu et al. |
| 9,119,965 B2 | 9/2015 | Xi et al. |
| 9,314,168 B2 | 4/2016 | Watson et al. |
| 9,395,792 B1 | 7/2016 | Kahn et al. |
| 10,349,212 B2* | 7/2019 | Tartz ......................... A61B 5/06 |
| 10,610,688 B2 | 4/2020 | Thakur et al. |
| 10,631,776 B2 | 4/2020 | Annoni et al. |
| 10,667,747 B2 | 6/2020 | Annoni et al. |
| 10,675,469 B2 | 6/2020 | Annoni et al. |
| 10,750,994 B2 | 8/2020 | Annoni et al. |
| 2004/0015091 A1 | 1/2004 | Greenwald et al. |
| 2005/0209643 A1* | 9/2005 | Heruth ..................... A61B 5/02 607/3 |
| 2007/0167859 A1 | 7/2007 | Finneran et al. |
| 2007/0213783 A1 | 9/2007 | Pless |
| 2007/0260285 A1 | 11/2007 | Libbus et al. |
| 2008/0077192 A1* | 3/2008 | Harry .................. A61N 1/0484 607/48 |
| 2008/0177191 A1 | 7/2008 | Patangay et al. |
| 2008/0249430 A1 | 10/2008 | John et al. |
| 2009/0192556 A1 | 7/2009 | Wu et al. |
| 2009/0312663 A1 | 12/2009 | John et al. |
| 2009/0318986 A1 | 12/2009 | Alo et al. |
| 2010/0016913 A1 | 1/2010 | Arcot-Krishnamurthy et al. |
| 2010/0286549 A1 | 11/2010 | John et al. |
| 2011/0015702 A1 | 1/2011 | Ternes et al. |
| 2011/0021928 A1 | 1/2011 | Giovangrandi et al. |
| 2011/0124979 A1 | 5/2011 | Heneghan et al. |
| 2011/0137134 A1 | 6/2011 | Hemmerling et al. |
| 2011/0172562 A1 | 7/2011 | Sahasrabudhe et al. |
| 2011/0224749 A1 | 9/2011 | Ben-David et al. |
| 2011/0306846 A1 | 12/2011 | Osorio |
| 2013/0165994 A1 | 6/2013 | Ternes et al. |
| 2013/0211291 A1* | 8/2013 | Tran ....................... G16H 50/20 600/595 |
| 2013/0268016 A1 | 10/2013 | Xi et al. |
| 2014/0276188 A1 | 9/2014 | Jardin |
| 2014/0276549 A1 | 9/2014 | Osorio |
| 2015/0005842 A1 | 1/2015 | Lee et al. |
| 2015/0289803 A1 | 10/2015 | Wu et al. |
| 2016/0022203 A1 | 1/2016 | Arnold et al. |
| 2016/0082265 A1 | 3/2016 | Moffitt et al. |
| 2016/0129272 A1 | 5/2016 | Hou et al. |
| 2016/0144194 A1 | 5/2016 | Roothans et al. |
| 2016/0243359 A1 | 8/2016 | Sharma |
| 2016/0302720 A1 | 10/2016 | John et al. |
| 2016/0350509 A1* | 12/2016 | Sharma .................... A61F 7/00 |
| 2016/0361515 A1* | 12/2016 | Jung ................... A61B 5/02055 |
| 2016/0374567 A1 | 12/2016 | Breslow et al. |
| 2018/0078768 A1 | 3/2018 | Thakur et al. |
| 2018/0085055 A1 | 3/2018 | Annoni et al. |
| 2018/0085584 A1 | 3/2018 | Thakur et al. |
| 2018/0110464 A1 | 4/2018 | Annoni et al. |
| 2018/0126169 A1* | 5/2018 | Hou ..................... A61N 1/36071 |
| 2018/0192941 A1 | 7/2018 | Annoni et al. |
| 2018/0193651 A1 | 7/2018 | Annoni et al. |
| 2020/0188673 A1 | 6/2020 | Thakur et al. |
| 2020/0214623 A1 | 7/2020 | Annoni et al. |
| 2020/0238087 A1 | 7/2020 | Annoni et al. |

FOREIGN PATENT DOCUMENTS

| | | |
|---|---|---|
| EP | 1897586 A1 | 3/2008 |
| EP | 3519037 B1 | 7/2020 |
| RU | 2559783 C1 | 8/2015 |
| WO | WO-2007007058 A1 | 1/2007 |
| WO | WO-2009055127 A1 | 4/2009 |
| WO | WO-2010051406 A1 | 5/2010 |
| WO | WO-2011008747 A2 | 1/2011 |
| WO | WO-2011053607 A1 | 5/2011 |
| WO | WO-2013134479 A1 | 9/2013 |
| WO | WO-2014151860 A1 | 9/2014 |
| WO | WO-2015060888 A1 | 4/2015 |
| WO | WO-2015128567 | 9/2015 |
| WO | WO-2016077786 A1 | 5/2016 |
| WO | WO-2018052695 A1 | 3/2018 |
| WO | WO-2018063637 A1 | 4/2018 |

(56) References Cited

FOREIGN PATENT DOCUMENTS

| WO | WO-2018063912 A1 | 4/2018 |
|---|---|---|
| WO | WO-2018080887 A1 | 5/2018 |

OTHER PUBLICATIONS

"International Application Serial No. PCT/US2017/048867, International Search Report dated Nov. 13, 2017", 5 pgs.
"International Application Serial No. PCT/US2017/048867, Written Opinion dated Nov. 13, 2017", 6 pgs.
"International Application Serial No. PCT/US2017/048896, International Search Report dated Nov. 27, 2017", 5 pgs.
"International Application Serial No. PCT/US2017/048896, Written Opinion dated Nov. 27, 2017", 6 pgs.
"International Application Serial No. PCT/US2017/052685, International Search Report dated Jan. 4, 2018", 5 pgs.
"International Application Serial No. PCT/US2017/052685, Written Opinion dated Jan. 4, 2018", 6 pgs.
"International Application Serial No. PCT/US2017/057367, International Search Report dated Jan. 19, 2018", 4 pgs.
"International Application Serial No. PCT/US2017/057367, Written Opinion dated Jan. 19, 2018", 4 pgs.
Ahern, David K., et al., "Comparison of lumbar paravertebral EMG patterns in chronic low back pain patients and non-patient controls", Pain, 34, (1988), 153-160.
Allum, John H.J., et al., "A speedy solution for balance and gait analysis: angular velocity measured at the centre of body mass", Current Opinion in Neurology 18, (2005), 15-21.
Alo, Kenneth M., et al., "Effect of Spinal Cord Stimulation on Sensory Nerve Conduction Threshold Functional Measures", Neuromodulation, vol. 3, No. 3, (2000), 145-154.
Ambady, Nalini, et al., "Thin Slices of Expressive Behavior as Predictors of Interpersonal Consequences: A Meta-Analysis", Psychological Bulletin, 1992, vol. 111, No. 2, 256-274.
Annoni, Elizabeth M., et al., "Method and Apparatus for Pain Management Using Objective Pain Measure", U.S. Appl. No. 62/400,336, filed Sep. 27, 2016.
Annoni, Elizabeth M., et al., "Pain Management Based on Brain Activity Monitoring", U.S. Appl. No. 62/445,061, filed Jan. 11, 2017.
Annoni, Elizabeth M., et al., "Pain Management Based on Muscle Tension Measurements", U.S. Appl. No. 62/445,092, filed Jan. 11, 2017.
Annoni, Elizabeth M., et al., "Pain Management Based on Respiration-Mediated Heart Rates", U.S. Appl. No. 62/445,069, filed Jan. 11, 2017.
Annoni, Elizabeth M., et al., "Patient-Specific Calibration of Pain Quantification", U.S. Appl. No. 62/445,095, filed Jan. 11, 2017.
Arsenault, Marianne, et al., "Pain Modulation Induced by Respiration: Phase and Frequency Effects", Neuroscience 252, (2013), 501-511.
Artner, Juraj, et al., "Prevalence of sleep deprivation in patients with chronic neck and back pain: a retrospective evaluation of 1016 patients", Journal of Pain Research: 6, (2013), 1-6.
Bakker, Jorn, et al., "What's your current stress level? Detection of stress patterns from GSR sensor data", Eindhoven University of Technology—The Netherlands, (2011), 1-8.
Baliki, Marwan N., et al., "Beyond Feeling: Chronic Pain hurts the Brain, Disrupting the Default-Mode Network Dynamics", The Journal of Neuroscience, 28 (6), (Feb. 6, 2008), 1398-1403.
Banos, Oresti, et al., "PhysioDroid: Combining Wearable Health Sensors and Mobile Devices for a Ubiquitous, Continuous, and Personal Monitoring", The Scientific World Journal, vol. 2014 Article ID 190824, (2014), 11 pgs.
Bansevicius, Dalius, et al., "Mental stress of long duration: EMG activity, perceived tension, fatigue, and pain development in pain-free subjects", Headache: The Journal of Head and Face Pain; 37.8, (1997), 499-510.

Barad, Meredith J., et al., "Complex Regional Pain Syndrome is Associated With Structural Abnormalities in Pain-Related Regions of the Human Brain", The Journal of Pain, vol. 15, No. 2, (Feb. 2914), 197-203.
Barkley, Jacob E., et al., "The effect of spinal cord stimulation unit revision on perceived pain, anxiety, mobility and physical activity in individuals with low back/lower extremity pain", Kent State University—The Spine and Pain Institute, Presented at Annual Meeting of the North American Neuromodulation Society (NANS) on Dec. 11-14, 2014, 1 pg.
Bartlett, Marian Stewart, et al., "Automatic Decoding of Facial Movements Reveals Deceptive Pain Expressions", Current Biology 24, 738-743, Mar. 31, 2014.
Beneck, George J., et al., "Spectral analysis of EMG using intramuscular electrodes reveals non-linear fatigability characteristics in persons with chronic low back pain", Journal of Electromyography and Kinesiology 23, (2013), 70-77.
Ben-Israel, Nir, et al., "Monitoring the nociception level: a multi-parameter approach", J Clin Monit Comput, (Jul. 2012), 10 pgs.
Ben-Israel, Nir, et al., "Monitoring the nociception level: a multi-parameter approach", J Clin Monit Comput 27, (2013), 659-668.
Berthomier, Christian, et al., "Automatic analysis of single-channel sleep EEG: validation in healthy individuals", Sleep—New York Then Westchester—30.11, (2007), 1587-1595.
Boselli, E., et al., "Prediction of immediate postoperative pain using the analgesia/nociception index: a prospective observational study", British Journal of Anaesthesia 112 (4):, (2014), 715-721.
Boselli, E., et al., "Prospective observational study of the non-invasive assessment of immediate postoperative pain using the analgesia/nociception index (ANI)", British Journal of Anaesthesia 111, (2013), 453-459.
Broucqsault-Dédrie, Celine, et al., "Measurement of Heart Rate Variability to Assess Pain in Sedated Critically Ill Patients: A Prospective Observational Study", PLOS One, (Jan. 25, 2016), 1-11.
Bunde, Armin, et al., "Correlated and uncorrelated regions in heart-rate fluctuations during sleep", Physical Review Letters 85.17, (2000), 3736-3739.
Chan, C. W.Y., et al., "Subjective pain sensation is linearly correlated with the Flexion reflex in man", Brain Research, 479, (1989), 145-150.
Chapman, C. Richard, et al., "Phasic pupil dilation response to noxious stimulation in normal volunteers: relationship to brain evoked potentials and pain report", (1999), 44-52.
Chen, Shuzhen, et al., "The role of the autonomic nervous system in hypertension: a bond graph model study", Physiological measurement 29.4 (2008): 473, (2008), 473-495.
Cheng, Qian, et al., "GaitTrack: Health Monitoring of Body Motion from Spatio-Temporal Parameters of Simple Smart Phones", The ACM Conference on Bioinformatics, Computational Biology, Biomed Biomedical Informatics (BCB) Health Information Symposium (HIS), Sep. 25, 2013,, (2013), 1-10.
Chuang, Chiung-Cheng, et al., "Photoplethysmography variability as an alternative approach to obtain heart rate variability information in chronic pain patient", J Clin Monit Comput—Published online, (Feb. 24, 2015), 1-6.
Chung, Ok Y., "Baroreflex sensitivity associated hypoalgesia in healthy states is altered by chronic pain", Pain 138, (2008), 87-97.
Ciampi De Andrade, Daniel, et al., "Neurophysiological assessment of spinal cord stimulation in failed back surgery syndrome", Pain 150, (2010), 485-491.
Cinaz, Burcu, et al., "Monitoring of mental workload levels during an everyday life office-work scenario", Pers Ubiquit Comput 17, (2013), 229-239.
Clark, Bryan Allen, et al., "Pain Management Based on Functional Measurements", U.S. Appl. No. 62/445,075, filed Jan. 11, 2017.
Culic, Ognjen, et al., "Serum activities of adenosine deaminase, dipeptidyl peptidase IV and prolyl endopeptidase in patients with fibromyalgia:diagnostic implications", Clin Rheumatol 35, (2016), 2565-2571.
Dansie, Elizabeth J., et al., "Activity in Adults with Chronic Widespread Pain", The Journal of Pain—Accepted Manuscript, (2014), 33 pgs.

(56) References Cited

OTHER PUBLICATIONS

Davydov, Dmitry M., et al., "Cardiovascular activity and chronic pain severity", Physiology & Behavior 152, 203-216 (2015).
De-La-Herran, Alvaro M., et al., "Gait Analysis Methods: An Overview of Wearable and Non-Wearable Systems, Highlighting Clinical Applications", Sensors 14, (2014), 3362-3394.
Denk, Franziska, et al., "Chronic Pain: Emerging Evidence for the Involvement of Epigenetics", Neuron 73 (3), (2012), 435-444.
Duschek, S., "Relationship between baroreceptor cardiac reflex sensitivity and pain experience in normotensive individuals", International Journal of Psychophysiology 65, (2007), 193-200.
Eisenberg, Elon, et al., "Quantitative Sensory Testing for Spinal Cord Stimulation in Patients With Chronic Neuropathic Pain", (2006), 161-165.
Elgendi, Mohamed, "On the analysis of fingertip photoplethysmogram signals", Current cardiology reviews 8.1, (2012), 14-25.
Evans, Subhadr, et al., "Heart rate variability as a biomarker for autonomic nervous system response differences between children with chronic pain and healthy control children", Journal of Pain Research 3.6, (2013), 449-457.
Fagius, J., et al., "The cold pressor test: effects on sympathetic nerve activity in human muscle and skin nerve fascicles", Acta physiologica Scandinavica 137.3, (1989), 325-334.
Fazalbhoy, Azharuddin, et al., "Individual differences in the cardiovascular responses to tonic muscle pain: parallel increases or decreases in muscle sympathetic nerve activity, blood pressure and heart rate", Exp Physiol 97.10, (2012), 1084-1092.
Foo, H., et al., "Brainstem modulation of pain during sleep and waking", Sleep medicine reviews 7.2, (2003), 145-154.
Frederiks, Joost, et al., "Within-subject electrocardiographic differences at equal heart rates: role of the autonomic nervous system", Pflugers Archiv 441.5, (2001), 717-724.
Geisser, Michael E., et al., "Pain-Related Fear, Lumbar Flexion, and Dynamic EMG Among Persons With Chronic Musculoskeletal Low Back Pain", Clin J Pain, vol. 20, No. 2, (Apr. 2004).
Generaal, Ellen, et al., "Reduced hypothalamic-pituitary-adrenal axis activity in chronic multi-site musculoskeletal pain: partly masked by depressive and anxiety disorders", BMC Musculoskeletal Disorders, 15:227, (2014), 1-11.
Gesche, Heiko, et al., "Continuous blood pressure measurement by using the pulse transit time: comparison to a cuff-based method", European journal of applied physiology 112.1, (2012), 309-315.
Godfrey, A., et al., "Direct measurement of human movement by accelerometry", Medical Engineering & Physics 30 (2008) 1364-1386.
Godfrey, A., et al., "Instrumenting gait with an accelerometer: a system and algorithm examination", Medical Engineering & Physics, Mar. 2015, doi:10.1016/j.medengphy.2015.02.003, 24 pgs.
Gouveia, S., et al., "Assessing Baroreflex Sensitivity in the Sequences Technique: Local versus Global Approach", Computers in Cardiology, 32, (2005), 279-282.
Granovsky, Yelena, et al., "Objective Correlate of Subjective Pain Perception by Contact Heat-Evoked Potentials", The Journal of Pain, vol. 9, No. 1, (Jan. 2008), 53-63.
Green, Alexande L., "Measurement of muscle sympathetic nerve activity reveals true sympathetic changes in chronic pain", Exp Physiol 97.10, (2012), 1083.
Hallman, David, et al., "Autonomic regulation, physical activity and perceived stress in subjects with musculoskeletal pain: 24-hour ambulatory monitoring", International Journal of Psychophysiology 86, (2012), 276-282.
Hallman, David M., et al., "Changes in physical activity and heart rate variability in chronic neck-shoulder pain: monitoring during work and leisure time", Int Arch Occup Environ Health 87, (2014), 735-744.
Hallman, David M., et al., "Long-Term Monitoring of Physical Behavior Reveals Different Cardiac Responses to Physical Activity among Subjects with and without Chronic Neck Pain", BioMed Research International, vol. 2015, Article ID 907482, 11 pages, http://dx.doi.org/10.1155/2015/907482, 11 pages.
Hartwich, Doreen, et al., "Effect of muscle metaboreflex activation on spontaneous cardiac baroreflex sensitivity during exercise in humans", J Physiol 589.24, (2011), 6157-6171.
Jensen, MP, et al., "Brain EEG activity correlates of chronic pain in persons with spinal cord injury: clinical implications", Nature; Spinal Cord; 51, (Jul. 17, 2012), 55-58.
Jess, Gunnar, et al., "Monitoring heart rate variability to assess experimentally induced pain using the analgesia nociception index—A randomised volunteer study", Eur J Anaesthesiol 32, (2015), 1-8.
Kang, Jon-Eun, et al., "Pulse transit time shows vascular changes caused by propofol in children", J Clin Monit Comput 29, (2015), 533-537.
Keefe, Francis J,, et al., "An Objective Approach to Quantifing Pain Behavior and Gait Patterns in Low Back Pain Patients", Pain, 21, (1985), 153-161.
Kemler, Marius A., et al., "Impact of Spinal Cord Stimulation on Sensory Characteristics in Complex Regional Pain Syndrome Type 1—A Randomized Trial", Anesthesiology, 95, (2001), 72-80.
Keshari, Kayvan R., et al., "Lactic Acid and Proteoglycans as Metabolic Markers dor Discogenic Back Pain", Spine, vol. 13, No. 3, (2008), 312-317.
Kim, Young Uk, et al., "Pulse Transit Time as a Predictor of the Efficacy of a Celiac Plexus Block in Patients With Chronic Intractable Abdominal Pain", Clin J Pain, vol. 32, No. 6, (Jun. 2015), 522-526.
Kodituwakku, Sandun, et al., "Point Process Respiratory Sinus Arrhythmia Analysis during Deep Tissue Pain Stimulation", Computing in Cardiology 38, (2011), 193-196.
Koenig, J., et al., "Heart rate variability and experimentally induced pain in healthy adults: A systematic review", European Journal of Pain 18, (2014), 301-314.
Koenig, Julian, et al., "Chronic Pain and Heart Rate Variability in a Cross-Sectional Occupational Sample Evidence for Impaired Vagal Control", The Clinical Journal of Pain, Publish Ahead of Print, (2015), 31 pgs.
La Rovere, Maria Teresa, et al., "Baroreflex Sensitivity: Measurement and Clinical Implications", Ann Noninvasive Electrodardiol, 13(2):191-207, 2008.
Lamoth, Claudine J.C., et al., "How do persons with chronic low back pain speed up and slow down? Trunk-pelvis coordination and erector spinae activity during gait", Gait & Posture 23, (2006), 230-239.
Lamoth, Claudine J.C., et al., "Pelvis-Thorax Coordination in the Transverse Plane During Walking in Persons With Nonspecific Low Back Pain", Spine, vol. 27, No. 4, (2002), E92-E99.
Lane, James D., et al., "Respiratory Sinus Arrhythmia and Cardiovascular Responses to Stress", Psychophysiology, vol. 29, No. 4, (1992), 461-470.
Latremoliere, Alban, et al., "Reduction of Neuropathic and Inflammatory Pain through Inhibition of the Tetrahydrobiopterin Pathway", Neuron, 86 (6), (2015), 1393-1406.
Ledowski, Thomas, et al., "The influence of age and sex on the relationship between heart rate variability, haemodynamic variables and subjective measures of acute post-operative pain", European Journal of Anaesthesiology, vol. 28, No. 6, (2011), 433-437.
Lee, Jihyoung, et al., "Validation of normalized pulse volume in the outer ear as a simple measure of sympathetic activity using warm and cold pressor tests: towards applications in ambulatory monitoring", Physiol. Meas. 34, (2013), 359-375.
Lidberg, Lars, et al., "Sympathetic Skin Nerve Dischai gcs in Relation lo Anipliliule ol Skin Resistance Responses", Psychophysiology, vol. 18, No. 3, (May 1981), 268-270.
Littlewort, Gwen C., et al., "Automatic Coding of Facial Expressions Displayed During Posed and Genuine Pain", Image and Vision Computing, 27(12) p. 1741-1844.
Logier, R., et al., "PhysioDoloris: a monitoring device for Analgesia / Nociception balance evaluation using Heart Rate Variability analysis", 32nd Annual International Conference of the IEEE EMBS, (2010), 1194-1197.
Looney, David, et al., "The In-the-Ear Recording Concept", IEEE Pulse Nov./Dec. 2012, 32-42.
March, Antonio, et al., "Pain Biomarkers", Clin Drug Invest, 29 Suppl 1, (2009), 41-46.

(56) References Cited

OTHER PUBLICATIONS

Martini, Chris H., et al., "Ability of the Nociception Level, a Multiparameter Composite of Autonomic Signals, to Detect Noxious Stimuli during Propofol-Remifentanil Anesthesia", Anesthesiology, vol. 123, No. 3, (2015), 524-534.
Mauer, C., et al., "Quantitative sensory testing in the German Research Network on Neuropathic Pain (DFNS): Somatosensory abnormalities in 1236 patients with different neuropathic pain syndromes", Pain 150, (2010), 439-450.
Mcbeth, John, et al., "Hypothalamic-pituitary-adrenal stress axis function and the relationship with chronic widespread pain and its antecedents", [Online]. Retrieved from the Internet: <URL: http://arthritis-research.com/content/7/5/R992, (2005), R992-R1000.
Mccarthy, K. F., et al., "Cerebrospinal fluid levels of glial cell-derived neurotrophic factor correlate with spinal cord stimulation frequency in patients with neuropathic pain: a preliminary report", Spinal Cord 52, (2014), S8-S10.
Mccracken, Lance M., et al., "Disrupted sleep patterns and daily functioning in patients with chronic pain", Pain Res Manage vol. 7 No. 2 Summer 2002 75-79.
Mikkelsen, Kaare B., et al., "EEGRecordedfromtheEar:CharacterizingtheEar-EEGMethod", FrontiersinNeuroscience|www.frontiersin.org, Nov. 2015|vol. 9|Article438, 8 pgs.
Mironer, Y. Eugene, et al., "Pain Tolerance Threshold: A Pilot Study of an Objective Measurement of Spinal Cord Stimulator Trial Results", Pain Medicine, vol. 1, No. 2, (2000), 110-115.
Moseley, G. Lorimer, et al., "Tactile Discrimination, but not tactile stimulation alone, reduces chronic limg pain", Pain 137, (2008), 600-608.
Moxham, I.M., "Understanding Arterial Pressure Waveforms", Southern African Journal of Anaesthesia and Analgesia 9.1, (2003), 40-42.
Mukkamala, R., et al., "Toward ubiquitous blood pressure monitoring via pulse transit time: theory and practice", IEEE Transactions on Biomedical Engineering 62.8, (2015), 1879-1901.
Mylius, Vett, et al., "Sex differences in nociceptive withdrawal reflex and pain perception", Somatosensory and Motor Research 22 (3), (Sep. 2005), 207-211.
Neblett, Randy, et al., "What Is the Best Surface EMG Measure of Lumbar Flexion-Relation for Distinguishing Chronic Low Back Pain Patients From Pain-Free Controls'?", Clin J Pain 29 (4)—NIH Public Access, (Apr. 2013), 334-340.
Ng, Joseph, et al., "EMG activity of trunk muscles and torque output during isometric axial rotation exertion: a comparison between back pain patients and matched controls", Journal of Orthopaedic Research; 20, (2002), 112-121.
Palermo, Tonya M., et al., "Subjective Sleep Disturbances in Adolescents With Chronic Pain: Relationship to Daily Functioning and Quality of Life", The Journal of Pain, vol. 6, No. 3, (Mar. 2995), 201-207.
Panjabi, Manohar, "Clinical spinal instability and low back pain", Journal of Electromyography and Kinesiology 13, (2003), 371-379.
Patti, Gary J., et al., "Metabolomics implicates altered sphingolipids in chronic pain of neuropathic origin", nature chemical biology, vol. 8, (Mar. 2012), 232-234.
Perruchoud, Christophe, et al., "Assessment of Physical Activity of Patients with Chronic Pain", Neuromodulation: Technology at the Neural Interface; 17, (2012), 42-47.
Pinheiro, Eulália Silva Dos Santos, et al., "Electroencephalographic Patterns in Chronic Pain: A Systematic Review of the Literature", PLOS ONE | DOI:10.1371/journal.pone.0149085 Feb. 25, 2016, 27 pgs.
Plaza-Manzano, Gustavo, et al., "Changes in Biochemical Markers of Pain Perception and Stress Response After Spinal Manipulation", Journal of Orthopaedic & Sports Physical Therapy, vol. 44, No. 4, (Apr. 2014), 231-239.
Pleger, Burkhard, et al., "Patterns of cortical reorginization parallel impaired tactile discrimination and pain intensity in complex regional pain syndrome", NeuroImage 32, (2006), 503-510.

Pluijms, Wouter A., et al., "Increased Contact Heat Evoked Potential Stimulation Latencies in Responders to Spinal Cord Stimulation for Painful Diabetic Cord Stimulation for Painful Diabetic Cord Stimulation for Painful Diabetic Polyneuropathy", Neuromodulation 18, (2015), 126-132.
Poon, C.C.Y., "Cuff-less and noninvasive measurements of arterial blood pressure by pulse transit time", 2005 IEEE Engineering in Medicine and Biology 27th Annual Conference. IEEE, 2006., (2006), 5877-5880.
Prichep, Leslie S., et al., "Evaluation of the Pain Matrix Using EEG Source Localization: A Feasibility Study", Pain Medicine 12, (2011), 1241-1248.
Prkachin, Kenneth, "The consistency of facial expressions of pain: a comparison across modalities", Pain, 51, (1992), 279-306.
Raminen, Tina, et al., "The Impact of Spinal Cord Stimulation on Sleep Patterns", Neuromodulation 19, (2016), 477-481.
Rasche, Dirk, et al., "Quantitative Sensory Testing in Patients With Chronic Unilateral Radicular Neuropathic Pain and Active Spinal Cord Stimulation", Neuromodulation, vol. 9, No. 3, (2006), 239-247.
Rhudy, Jamie L., et al., "Defining the nociceptive flexion reflex (NFR) threshold in human participants: A comparison of different scoring criteria", Pain 128, (2007), 244-253.
Roy, Sourav Dey, et al., "An Approach for Automatic Pain Detection through Facial Expression", Procedia Computer Science 84 (2016) 99-106.
Sacco, Marcella, et al., "The Relationship Between Blood Pressure and Pain", The Journal of Clinical Hypertension vol. 15, No. 8, (Aug. 2013), 600-605.
Sano, Akane, et al., "Quantitative analysis of wrist electrodermal activity during sleep", Int J Psychophysiol. Dec. 2014 ; 94(3), (2014), 382-389.
Sarnthein, Johannes, et al., "Increased EEG power and slowed dominant frequncy in patients with neurogenic pain", Brain 129, (2005), 55-64.
Sato, Karina L/, et al., "Spinal Cord Stimulation (SCS) Improves Decreased Physical Activity Induced by Nerve Injury", Behavioral Neuroscience, vol. 128, No. 5, (2914), 625-632.
Sawada, Yukihiro, et al., "Normalized pulse volume (NPV) derived photo-plethysmography as a more valid measure of the finger vascular tone", International Journal of Psychophysiology 41, (2001), 1-10.
Sayar, Kemal, et al., "Sleep Quality in Chronic Pain Patients", Can J. Psychiatry, vol. 47, No. 9, (Nov. 2002), 844-848.
Schulman, Joshua J., et al., "Thalamocortical dysrhythmia syndrome: MEG imaging of neuropathic pain", (Jul. 25, 2014), 33-39.
Schulz, Enrico, et al., "Prefrontal Gamma Oscillations Encode Tonic Pain in Humans", Cerebral Cortex 2015, (Mar. 8, 2015), 1-8.
Sesay, MUSA, et al., "Responses of Heart Rate Variability to Acute Pain After Minor Spinal Surgery: Optimal Thresholds and Correlation With the Numeric Rating Scale", J Neurosurg Anesthesiol, vol. 00, No. 00, (2014), 1-7.
Shouldice, R., "PR and PP ECG intervals as indicators of autonomic nervous innervation of the cardiac sinoatrial and atrioventricular nodes", Neural Engineering, 2003. Conference Proceedings. First International IEEE EMBS Conference on. IEEE, (Mar. 2003), 261-264.
Siddall, Phillip J., et al., "Magnetic Resonance Spectroscopy Detects Biochemical Changes in the Brain Associated with Chronic Low Back Pain: A Preliminary Report", Anesth Analg 102, (2006), 1164-1168.
Sihvonen, T., et al., "Electric behavior of low back muscles during lumbar pelvic rhythm in low back pain patients and healthy controls", Archives of physical medicine and rehabilitation; 72.13, (1991), 1080-1087.
Simoes, Mario A., "Feasibility of Wearable Sensors to Determine Gait Parameters", University of South Florida Scholar Commons, (2011), 1-98.
Skljarevski, V., et al., "The nociceptive flexion reflex in humans—review article", Pain, 96, (2002), 3-8.
Smallwood, Rachel F., et al., "Structural Brain Anomalies and Chronic Pain: A Quantitative Meta-Analysis of Gray Matter Volume", The Journal of Pain, vol. 14, No. 7, (Jul. 2013), 663-675.

(56) References Cited

OTHER PUBLICATIONS

Srivastava, Kyle Harish, et al., "Pain Management Based on Cardiovascular Parameters", U.S. Appl. No. 62/445,053, filed Jan. 11, 2017.
Srivastava, Kyle Harish, et al., "Pain Management Based on Emotional Expression Measurements", U.S. Appl. No. 62/445,082, filed Jan. 11, 2017.
Staud, Roland, "Heart rate variability as a biomarker of fibromyalgia syndrome", Fut Rheumatol 3 (5)—NIH Public Access, (Oct. 1, 2008), 475-483.
Storm, H., et al., "Skin conductance correlates with perioperative stress", Acta Anaesthesiol Scand 46, (2002), 887-895.
Sturgeon, John A., et al., "Respiratory Sinus Arrhythmia: a Marker of Resilience to Pain Induction", Int.J. Behav. Med. 21, (2014), 961-965.
Swenne, C. A., "Baroreflex sensitivity: mechanisms and measurement", Neth Heart J 21, (2013), 58-60.
Symons, Frank J., et al., "Can Biomarkers Differentiate Pain and No Pain Subgroups of Nonverbal Children with Cerebral Palsy? A Preliminary Investigation Based on Noninvasive Saliva Sampling", Pain Med 16 (2), (2015), 249-256.
Tagliazucchi, Enzo, et al., "Brain resting state is disrupted in chronic back pain patients", Neurosci Lett. 485 (1)—NIH Public Access, (Nov. 12, 2010), 26-31.
Tao, Weijun, et al., "Gait Analysis Using Wearable Sensors", Sensors 12, (2012), 2255-2283.
Tauda, Makoto, et al., "P2X4receptorsandneuropathicpain", Frontiers in Cellular Neuroscience, vol. 7, Article 191, (Oct. 28, 2013), 1-6.
Terkelsen, Astrid J., et al., "Heart Rate Variability in Complex Regional Pain Syndrome during Rest and Mental and Orthostatic Stress", Anesthesiology, vol. 116, No. 1, (Jan. 2012), 133-146.
Thakur, Pramodsingh Hirasingh, et al., "Method and Apparatus for Pain Control Using Baroreflex Sensitivity During Posture Change", U.S. Appl. No. 62/412,587, filed Oct. 25, 2016.
Thakur, Pramodsingh Hirasingh, et al., "Systems and Methods for Closed-Loop Pain Management", U.S. Appl. No. 62/400,313, filed Sep. 27, 2016.
Thankur, Pramodsingh Hirasingh, et al., "Method and Apparatus for Pain Management Using Heart Sounds", U.S. Appl. No. 62/395,641, filed Sep. 16, 2016.
Theuvenel, Peter J., et al., "Responses to Median and Tbial Nerve Stimulation in Patients with Chronic Neuropathic Pain", Brain Topography, vol. 11, No. 4, (1999), 306-313.
Uceyler, Nuncan, et al., "Differential expression of cytokines in painful and painless neuropathies", (2007).
Uzar, E., et al., "Serum cytokine and pro-brain natriuretic peptide (BNP) levels in patients with migraine", European Review for Medical and Pharmacological Sciences; 15, (2011), 1111-1116.
Van Velzen, Marit H.N., et al., "Effect of heat-induced pain stimuli on pulse transit time and pulse wave amplitude in healthy volunteers", Physiological Measurement 37, (2016), 52-66.
Villarejo, Viqueira Maria, et al., "A Stress Sensor Based on Galvanic Skin Response (GSR) Controlled by ZigBee", Sensors 12, (2012), 6075-6101.
Walton, K. D., et al., "Abnormal thalamocortical activity in patients with Complex Regional Pain Syndrome (CRPS) Type 1", Pain 150, (2010), 41-51.
Willer, Jean Claude, "Comparative Study of Perceived Pain and Nociceptive Flexion Reflex in Man", Pain, 3, (1977), 69-80.
Williams, Dewayne P., et al., "Effects of Chronic Pelvic Pain on Heart Rate Variability in Women", The Journal of Urology, vol. 194 (Nov. 2015), 1-6.
Wong, Arnold Y.L., et al., "Does experimental low back pain change posteroanterior lumbar spinal stiffness and trunk muscle activity? A randomized crossover study", Clinical Biomechanics 34, (2016), 45-52.
Wong, Jih-Sen, et al., "A comparative study of pulse rate variability and heart rate variability in healthy subjects", J Clin Monit Comput 26, (2012), 107-114.
Wu, Hao-Yu, et al., "Eulerian Video Magnification for Revealing Subtle Changes in the World", ACM Transactions on Graphics 31, No. 4, (Jul. 1, 2012), 1-8.
Zamuner, Antonio R., et al., "Respiratory Sinus Arrhythmia and its Association with Pain in Women with Fibromyalgia Syndrome", Pain Practice, vol. 16, Issue 6, (2016), 704-711.
Zamunér, A. R., et al., "Relationship between sympathetic activity and pain intensity in fibromyalgia", Clin Exp Rheumatol 33—Abstract, [Online]. Retrieved from the Internet: <URL: http://www.ncbi.nlm.nih.gov.ezp3.lib.umn.edu/pubmed/25786044, (Feb. 2015), 1-2.
Zeng, Zhihong, et al., "A Survey of Affect Recognition Methods: Audio, Visual and Spontaneous Expressions", ICMI'07, Nov. 12-15, 2007, 126-133.
Zhang, John, "Effect of Chiropractic Care on Heart Rate Variability and Pain in a Multisite Clinical Study", Jimmal of Manipulative and Physiological Therapeutics, vol. 29, No. 4, (2006), 267-274.
Zhou, Jing, et al., "Recurrent Convolutional Neural Network Regression for Continuous Pain Intensity Estimation in Video", arXiv preprint arXiv:1605.00894 (2016) 84-92.
Zhou, Jing, et al., "Recurrent Convolutional Neural Network Regression for Continuous Pain Intensity Estimation in Video", Technical Report, (May 3, 2016), 1-11.
"U.S. Appl. No. 15/687,925, Final Office Action dated Feb. 14, 2019", 10 pgs.
"U.S. Appl. No. 15/687,925, Non Final Office Action dated Jun. 11, 2019", 11 pgs.
"U.S. Appl. No. 15/687,925, Non Final Office Action dated Oct. 9, 2018", 9 pgs.
"U.S. Appl. No. 15/687,925, Response filed Jan. 9, 2019 to Non Final Office Action dated Oct. 9, 2018", 9 pgs.
"U.S. Appl. No. 15/687,925, Response filed May 13, 2019 to Final Office Action dated Feb. 14, 2019", 11 pgs.
"U.S. Appl. No. 15/688,676, Examiner Interview Summary dated Sep. 25, 2019", 3 pgs.
"U.S. Appl. No. 15/688,676, Final Office Action dated Jul. 29, 2019", 7 pgs.
"U.S. Appl. No. 15/688,676, Non Final Office Action dated Jan. 11, 2019", 7 pgs.
"U.S. Appl. No. 15/688,676, Non Final Office Action dated Oct. 30, 2019", 6 pgs.
"U.S. Appl. No. 15/688,676, Response filed Sep. 25, 2019 to Final Office Action dated Jul. 29, 2019", 10 pgs.
"U.S. Appl. No. 15/688,676, Response filed Apr. 9, 2019 to Non Final Office Action dated Jan. 11, 2019", 12 pgs.
"U.S. Appl. No. 15/711,578, Examiner Interview Summary dated Aug. 28, 2019", 3 pgs.
"U.S. Appl. No. 15/711,578, Non Final Office Action dated May 23, 2019", 6 pgs.
"U.S. Appl. No. 15/711,578, Repsonse filed Aug. 23, 2019 to Non Final Office Action dated May 23, 2019", 11 pgs.
"U.S. Appl. No. 15/711,578, Supplemental Response filed Aug. 28, 2019 to Non Final Office Action dated May 23, 2019", 11 pgs.
"U.S. Appl. No. 15/788,403, Non Final Office Action dated Jul. 23, 2019", 9 pgs.
"U.S. Appl. No. 15/788,403, Response filed Oct. 8, 2019 to Non Final Office Action dated Jul. 23, 2019", 11 pgs.
"U.S. Appl. No. 15/867,756, Examiner Interview Summary dated Aug. 28, 2019", 3 pgs.
"U.S. Appl. No. 15/867,756, Non Final Office Action dated Jul. 1, 2019", 8 pgs.
"U.S. Appl. No. 15/867,756, Response filed Aug. 29, 2019 to Non Final Office Action dated Jul. 1, 2019", 11 pgs.
"U.S. Appl. No. 15/867,801, Non Final Office Action dated Sep. 30, 2019", 10 pgs.
"Australian Application Serial No. 2017325823, First Examination Report dated Jun. 19, 2019", 3 pgs.
"Australian Application Serial No. 2017334841, First Examination Report dated Jun. 24, 2019", 3 pgs.
"Australian Application Serial No. 2017335497, First Examination Report dated Jun. 26, 2019", 3 pgs.

(56) References Cited

OTHER PUBLICATIONS

"International Application Serial No. PCT/US2017/048867, International Preliminary Report on Patentability dated Mar. 28, 2019", 8 pgs.

"International Application Serial No. PCT/US2017/048896, International Preliminary Report on Patentability dated Apr. 11, 2019", 8 pgs.

"International Application Serial No. PCT/US2017/052685, International Preliminary Report on Patentability dated Apr. 11, 2019", 6 pgs.

"International Application Serial No. PCT/US2017/057367, International Preliminary Report on Patentability dated May 9, 2019", 6 pgs.

"International Application Serial No. PCT/US2018/013257, International Preliminary Report on Patentability dated Jul. 25, 2019", 8 pgs.

"International Application Serial No. PCT/US2018/013257, International Search Report dated Apr. 19, 2018", 4 pgs.

"International Application Serial No. PCT/US2018/013257, Written Opinion dated Apr. 19, 2018", 6 pgs.

"U.S. Appl. No. 15/688,676, Response filed Jan. 7, 2020 to Non Final Office Action dated Oct. 30, 2019", 10 pgs.

"U.S. Appl. No. 15/711,578, Notice of Allowance dated Nov. 25, 2019", 7 pgs.

"U.S. Appl. No. 15/788,403, Notice of Allowance dated Jan. 23, 2020", 7 pgs.

"U.S. Appl. No. 15/867,756, Notice of Allowance dated Dec. 19, 2019", 7 pgs.

"U.S. Appl. No. 15/867,801, Notice of Allowance dated Feb. 5, 2020", 8 pgs.

"U.S. Appl. No. 15/867,801, Response filed Dec. 18, 2019 to Non Final Office Action dated Sep. 30, 2019", 12 pgs.

"Australian Application Serial No. 2017334841, Response filed Feb. 6, 2020 to First Examination Report dated Jun. 24, 2019", 14 pgs.

"Australian Application Serial No. 2017335497, Response filed Nov. 27, 2019 to First Examination Report dated Jun. 26, 2019", 18 pgs.

"European Application Serial No. 17762308.9, Response to Communication pursuant to Rules 161 & 162 filed Nov. 26, 2019", 23 pgs.

"European Application Serial No. 17778108.5, Response to Communication Pursuant to Rules 161 and 162 filed Dec. 2, 2019", 3 pgs.

"European Application Serial No. 17794503.7, Response to Communication Pursuant to Rules 161 and 162 filed Dec. 30, 2019", 11 pgs.

"U.S. Appl. No. 15/688,676, Notice of Allowance dated Apr. 14, 2020", 7 pgs.

"U.S. Appl. No. 15/788,403, 312 Amendment filed Apr. 22, 2020", 8 pgs.

"U.S. Appl. No. 15/788,403, Corrected Notice of Allowability dated Mar. 18, 2020", 2 pgs.

"U.S. Appl. No. 15/788,403, PTO Response to Rule 312 Communication dated Apr. 30, 2020", 2 pgs.

"European Application Serial No. 18701908.8, Communication Pursuant to Article 94(3) EPC dated May 20, 2020", 6 pgs.

"European Application Serial No. 18701908.8, Response to Communication Pursuant to Rules 161 and 162 filed Mar. 16, 2020", 8 pgs.

\* cited by examiner

METHOD AND APPARATUS FOR PAIN MANAGEMENT WITH SLEEP DETECTION

CLAIM OF PRIORITY

This application claims the benefit of priority under 35 U.S.C. § 119(e) of U.S. Provisional Patent Application Ser. No. 62/457,456, filed on Feb. 10, 2017, which is herein incorporated by reference in its entirety.

TECHNICAL FIELD

This document relates generally to medical devices and more particularly to a pain management system that determines sleep state and control pain management based on the sleep state.

BACKGROUND

Pain may result from an injury, a disease (e.g., arthritis, fibromyalgia), or even a medical treatment (e.g., certain cancer treatment). Various treatments are applied for pain management, such as medication, psychotherapy, electrical stimulation, thermal therapy, and their various combinations. Examples of electrical stimulation for pain management include Transcutaneous Electrical Nerve Stimulation (TENS) delivered by a TENS unit and Spinal Cord Stimulation (SCS) that may be delivered by an implantable neuromodulation systems. Pain treatment may be prescribed based on an assessment of a patient's symptoms and underlying conditioning and titrated based on the patient's response to the treatment. As pain is not directly measurable by a machine, the assessment of the condition and the titration of the therapy may depend on questioning the patient. Because pain is affected by various factors, such as physical, physiological, and mental states of the patient, that vary with time, dependency on patient feedback limits timely adjustment or optimization of a pain suppression therapy.

SUMMARY

An Example (e.g., "Example 1") of a system for providing a patient with pain management may include a sleep monitoring circuit, a pain relief device, and a control circuit. The sleep monitoring circuit may be configured to sense one or more sleep signals from the patient and to determine a sleep state of the patient using the one or more sleep signals. The one or more sleep signals may include one or more physiological signals corresponding to the sleep state of the patient. The pain relief device may be configured to deliver one or more pain relief therapies. The control circuit may be configured to control the delivery of the one or more pain relief therapies using therapy parameters and to adjust the therapy parameters based on the determined sleep state.

In Example 2, the subject matter of Example 1 may optionally be configured to include an implantable medical device that includes at least portions of the sleep monitoring circuit, the pain relief device, and the control circuit.

In Example 3, the subject matter of any one or any combination of Examples 1 and 2 may optionally be configured such that the pain relief device includes a neurostimulator configured to deliver neurostimulation, and the control circuit is configured to control the delivery of the neurostimulation using stimulation parameters and adjust the stimulation parameters based on the determined sleep state.

In Example 4, the subject matter of any one or any combination of Examples 1 to 3 may optionally be configured such that the sleep monitoring circuit includes one or more sleep sensors configured to sense the one or more sleep signals from the patient, a sleep signal sensing circuit configured to process the one or more sleep signals, a sleep parameter generator circuit configured to generate one or more sleep parameters corresponding to the sleep state of the patient using the processed one or more sleep signals, and a sleep analyzer circuit to determine the sleep state of the patient using the generated one or more sleep parameters and a predetermined relationship between values of the one or more sleep parameters and the sleep state of the patient.

In Example 5, the subject matter of Example 4 may optionally be configured such that the one or more sleep sensors include one or more implantable sensors.

In Example 6, the subject matter of any one or any combination of Examples 4 and 5 may optionally be configured such that the one or more sleep sensors include one or more externally wearable sensors.

In Example 7, the subject matter of any one or any combination of Examples 4 to 6 may optionally be configured such that the sleep analyzer circuit includes a sleep parameter analyzer circuit configured to receive and analyze the generated one or more sleep parameters and a sleep score generator circuit configured to compute a sleep score using an outcome of the analysis of the generated one or more sleep parameters. The sleep score is indicative of the sleep state of the patient and includes one or more of a number, a sleep signal metric, or a number being a function of the sleep signal metric. The control circuit is configured to adjust the therapy parameters using the computed sleep score.

In Example 8, the subject matter of any one or any combination of Examples 4 to 7 may optionally be configured to further include a pain monitoring circuit configured to receive and analyze the sleep state and one or more of a physiological parameter indicative of a physiological function or physiological state of the patient, a functional parameter indicative of a physical activity or physical state of the patient, or a patient parameter including subjective information provided by the patient and to compute a pain score using an outcome of the analysis. The pain score indicates a degree of the pain of the patient. The control circuit is configured to adjust the therapy parameters using the pain score.

In Example 9, the subject matter of any one or any combination of Examples 4 to 8 may optionally be configured such that the one or more sleep sensors include a three-axis accelerometer configured to sense an accelerometer signal of the one or more sleep signals.

In Example 10, the subject matter of any one or any combination of Examples 4 to 9 may optionally be configured such that the one or more sleep sensors include a three-axis gyroscope configured to sense a gyroscope signal of the one or more sleep signals.

In Example 11, the subject matter of any one or any combination of Examples 4 to 10 may optionally be configured such that the one or more sleep sensors include an electrocardiogram (ECG) sensor configured to sense an ECG signal of the one or more sleep signals.

In Example 12, the subject matter of any one or any combination of Examples 4 to 11 may optionally be configured such that the one or more sleep sensors include an electroencephalogram (EEG) sensor configured to sense an EEG signal of the one or more sleep signals.

In Example 13, the subject matter of any one or any combination of Examples 4 to 12 may optionally be configured such that the one or more sleep sensors include a temperature sensor configured to sense a temperature signal of the one or more sleep signals.

In Example 14, the subject matter of any one or any combination of Examples 4 to 13 may optionally be configured such that the one or more sleep sensors include an electrodermal activity (EDA) sensor configured to sense an EDA signal of the one or more sleep signals.

In Example 15, the subject matter of any one or any combination of Examples 4 to 14 may optionally be configured such that the one or more sleep sensors include a blood volume pulse (BVP) sensor configured to sense a BVP signal of the one or more sleep signals.

An example (e.g., "Example 16") of a method for providing a patient with pain management is also provided. The method may include sensing one or more sleep signals from the patient, determining the sleep state of the patient using the one or more sleep signals, controlling the delivery of one or more pain relief therapies using therapy parameters, adjusting the therapy parameters based on the determined sleep state, and delivering the one or more pain relief therapies. The one or more sleep signals may include one or more physiological signals corresponding to a sleep state of the patient.

In Example 17, the subject matter of determining the sleep state as found in Example 16 may optionally further include determining a sleep stage.

In Example 18, the subject matter of delivering the one or more pain relief therapies as found in Example 17 may optionally further include delivering neurostimulation, and the subject matter of adjusting the therapy parameters based on the determined sleep state as found in Example 17 may optionally further include adjusting stimulation parameters based on the determined sleep stage.

In Example 19, the subject matter of determining the sleep stage as found in any one or any combination of Examples 17 and 18 may optionally further include producing a sleep score using the one or more sleep signals, and the subject matter of adjusting the therapy parameters based on the determined sleep state as found in any one or any combination of Examples 17 and 18 may optionally further include adjusting the therapy parameters based on the produced sleep score. The sleep score is indicative of the sleep stage and includes one or more of a number, a sleep signal metric, or a number being a function of the sleep signal metric.

In Example 20, the subject matter of any one or any combination of Examples 16 to 19 may optionally further include receiving and analyzing the determined sleep state and one or more of a physiological parameter indicative of a physiological function or physiological state of the patient, a functional parameter indicative of a physical activity or physical state of the patient, or a patient parameter including subjective information provided by the patient and to compute a pain score using an outcome of the analysis, the pain score indicating a degree of the pain of the patient, and the subject matter of adjusting the therapy parameters based on the determined sleep state as found in any one or any combination of Examples 16 to 19 may optionally include adjusting the therapy parameters based on the pain score.

In Example 21, the subject matter of sensing the one or more sleep signals from the patient as found in any one or any combination of Examples 16 to 20 may optionally further include sensing one or more of an accelerometer signal, a gyroscope signal, an electrocardiogram (ECG) signal, an electroencephalogram (EEG) signal, a temperature signal of the one or more sleep signals, an electrodermal activity (EDA) signal, a blood volume pulse (BVP) signal, or a bioelectric impedance signal.

In Example 22, the subject matter of delivering one or more pain relief therapies as found in any one or any combination of Examples 16 to 21 may optionally further include delivering the one or more pain relief therapies from a medical device implanted in the patient or externally worn by the patient.

In Example 23, the subject matter of sensing the one or more sleep signals as found in any one or any combination of Examples 16 to 22 may optionally further include sensing at least one sleep signal of the one or more sleep signals using a sensor implanted in the patient.

In Example 24, the subject matter of sensing the one or more sleep signals as found in any one or any combination of Examples 16 to 23 may optionally further include sensing at least one sleep signal of the one or more sleep signals using a sensor externally worn by the patient.

In Example 25, the subject matter of sensing the one or more sleep signals as found in any one or any combination of Examples 22 to 24 may optionally further include sensing at least one sleep signal of the one or more sleep signals using a sensor communicatively coupled to the medical device via a wireless link.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
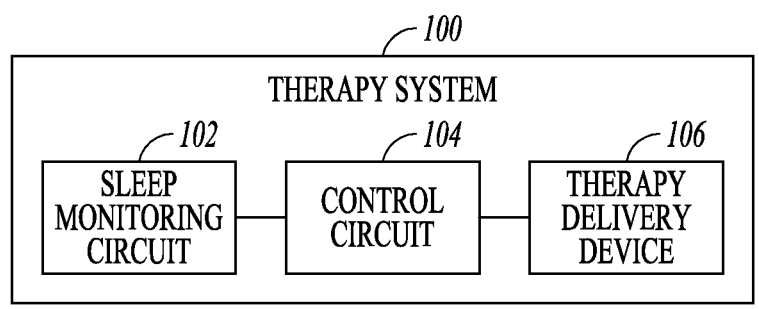
FIG. 1 illustrates an embodiment of a therapy system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a system for controlling delivery of a therapy to a patient based on sleep state of the patient. Conditions, such as chronic pain, can be affected by the patient's sleep state and quality, and also affects the patient's sleep state and quality. Chronic therapies, such as a therapy for controlling chronic pain, needs optimization of settings during wakefulness that differ from those during sleep to maximize its therapeutic benefits to the patient. Sleep quality is an important therapeutic outcome and is associated with the patient's overall health status. However, it is not often measured and used in demonstrating therapeutic efficacy. For example, to control delivery of a pain suppression therapy automatically using a closed-loop system, there is a need to use the patient's sleep state as an input and/or as a measure of efficacy of the therapy.

Physiological conditions during sleep differ greatly from those during wakefulness, and thus treatment for chronic diseases must reflect those changes. For instance, in a chronic pain patient treated with spinal cord stimulation, levels of endogenous neurotransmitters during sleep may require lesser stimulation current to achieve pain reduction. In an algorithm designed to objectively measure pain, it would be important to distinguish changes in physiological parameters due to sleep changes compared to those due to pain. Because chronic pain patients often report disturbances with their sleep, stages and quality of sleep can be used as a surrogate for pain levels for controlling therapy delivery. Modulating therapy using the patient's sleep state can also save battery energy in an implantable device delivering a pain suppression therapy because less stimulation energy is needed during sleep.

Wakefulness can be differentiated from sleep using a range of different modalities, including electroencephalography (EEG), electrodermal activity (EDA), and heart rate. These modalities can be used to differentiate various stages of sleep. For example, studies showed that sleep epochs with EDA peaks are more common during slow-wave sleep than in rapid eye movement (REM) sleep.

Chronic pain patients are more likely than a healthy person to suffer from poor sleep quality and disturbances during sleep. Greater sleep disturbance was shown to be correlated to greater pain intensity, disability, depression, and physical symptoms. Often it is considered that sleep disruption is a consequence of pain. However, this in fact can be a bidirectional relation. Sleep, emotional distress, pain perception, daily physical activity appear to link to each other to form a cycle in the patient's daily experience.

In 2015, the National Sleep Foundation conducted a "Sleep in America Poll", which resulted in a finding that pain was the main factor between the amounts of sleep people said they needed and how much they got (sleep gap), with chronic pain having a larger discrepancy than those with acute pain. In addition, pain, stress, and poor health were the key correlates of shorter sleep durations and worse sleep quality. However, for those who make sleep a priority, the sleep gap narrows sharply and is associated with less stress and better health.

The present system can include a therapeutic medical device, such as a spinal cord stimulator or intrathecal drug pump, that monitors physiological signals from wearable and/or implantable sensors to determine a patient's stages of sleep and controls delivery of a therapy based on the stage of sleep. In various embodiments, the stage of sleep can be used as an input signal in an automated closed-loop therapy control system and/or as a guide for a user adjusting the therapy. In this document, a "user" can include a physician or other care provider who treats the patient using the present system. While pain management is discussed as a specific example of application, the present subject matter can be applied in controlling and/or optimizing any therapy based on sleep states. For example, the present subject matter can also be used to control and/or optimize a therapy for improving sleep (e.g., a spinal cord stimulation therapy) that potentially provides a more natural human sleep pattern, increased rapid eye movement (REM) sleep, etc.

FIG. 1 illustrates an embodiment of a therapy system 100 for delivering one or more therapies to a patient and controlling the delivery of the one or more therapies based on the patient's sleep state. Therapy system 100 can include a sleep monitoring circuit 102, a control circuit 104, and a therapy delivery device 106. Sleep monitoring circuit 102 can sense one or more sleep signals from the patient, and can determine the sleep state of the patient using the one or more sleep signals. The one or more sleep signals can include one or more physiological signals corresponding to (or indicative of) the sleep state of the patient. The sleep state can include a sleep stage and/or one or more indicators of sleep quality such as time spent at each sleep stage and/or percentage of the time spent at each sleep stage during a sleeping period. Therapy delivery device 106 can deliver the one or more therapies for treating one or more pathological conditions in which sleep is an important factor, and/or in which improved sleep is a desirable outcome. For example, the one or more therapies may target at pain suppression and/or sleep quality improvement. Control circuit 104 can control the delivery of the one or more therapies from therapy delivery device 106 using therapy parameters and adjust the therapy parameters based on the sleep state. In various embodiments, control circuit 106 can optimize the therapy parameters for the determined sleep state. In various embodiments, control circuit 104 can execute a closed-loop therapy algorithm for treating the one or more pathological conditions using the determined sleep state as an input.

In various embodiments, circuits of system 100, including its various embodiments discussed in this document, may be implemented using a combination of hardware and software. For example, sleep monitoring circuit 102 and control circuit 104, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 2:
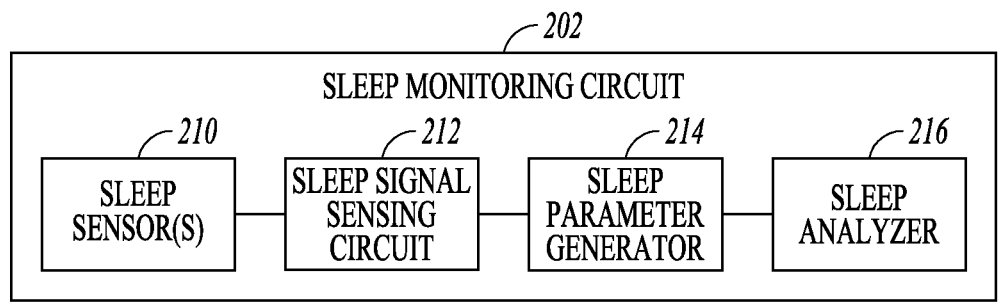
FIG. 2 illustrates an embodiment of a sleep monitoring circuit, such as may be used in the therapy system of FIG. 1.

FIG. 2 illustrates an embodiment of a sleep monitoring circuit 202, which represents an example of sleep monitoring circuit 102. Sleep monitoring circuit 202 can include one or more sleep sensors 210, a sleep signal sensing circuit 212, a sleep parameter generator (or sleep parameter generator circuit) 214, and a sleep analyzer (or sleep analyzer circuit) 216. Sleep sensor(s) 210 can sense the one or more sleep signals from the patient. In various embodiments, sleep sensor(s) 210 can include one or more sensors each being incorporated into a medical device such as a medical device that includes control circuit 104 and therapy delivery device 106 or being another device communicatively coupled to the medical device via a wired or wireless communication link. In various embodiments, sleep sensor(s) 210 can include one or more sensors each being an implantable sensor or an externally wearable (non-implantable) sensor. The implantable sensor can be, for example, part of an implantable medical device that can include control circuit 104 and therapy delivery device 106 or being another implantable device communicatively coupled to the implantable medical device via a wired or wireless communication link. The externally wearable sensor can be, for example, part of an externally wearable medical device that can include control circuit 104 and therapy delivery device 106, being another externally wearable device communicatively coupled to the externally wearable medical device via a wired or wireless communication link, or being an externally wearable device communicatively coupled to an implantable medical device that includes control circuit 104 and therapy delivery device 106 via a wired or wireless communication link. Sleep signal sensing circuit 212 can process the one or more sleep signals, such as by filtering and/or amplifying each sensed sleep signal. Sleep parameter generator 214 can generate one or more sleep parameters corresponding to (or indicative of) the sleep state of the patient using the processed one or more sleep signals. For example, sleep parameter generator 214 can detect specified features in each sensed sleep signal, measuring amplitude and/or time associated with the detected features, and generate one or more sleep parameters using results of the measurement. Sleep analyzer 216 can determine the sleep state of the patient using the one or more sleep parameters generated by sleep parameter generator 214. Thus, the sleep state can be indicated by using information extracted from the one or more sleep signals sensed using one or more sensors 210.

Figure 3:
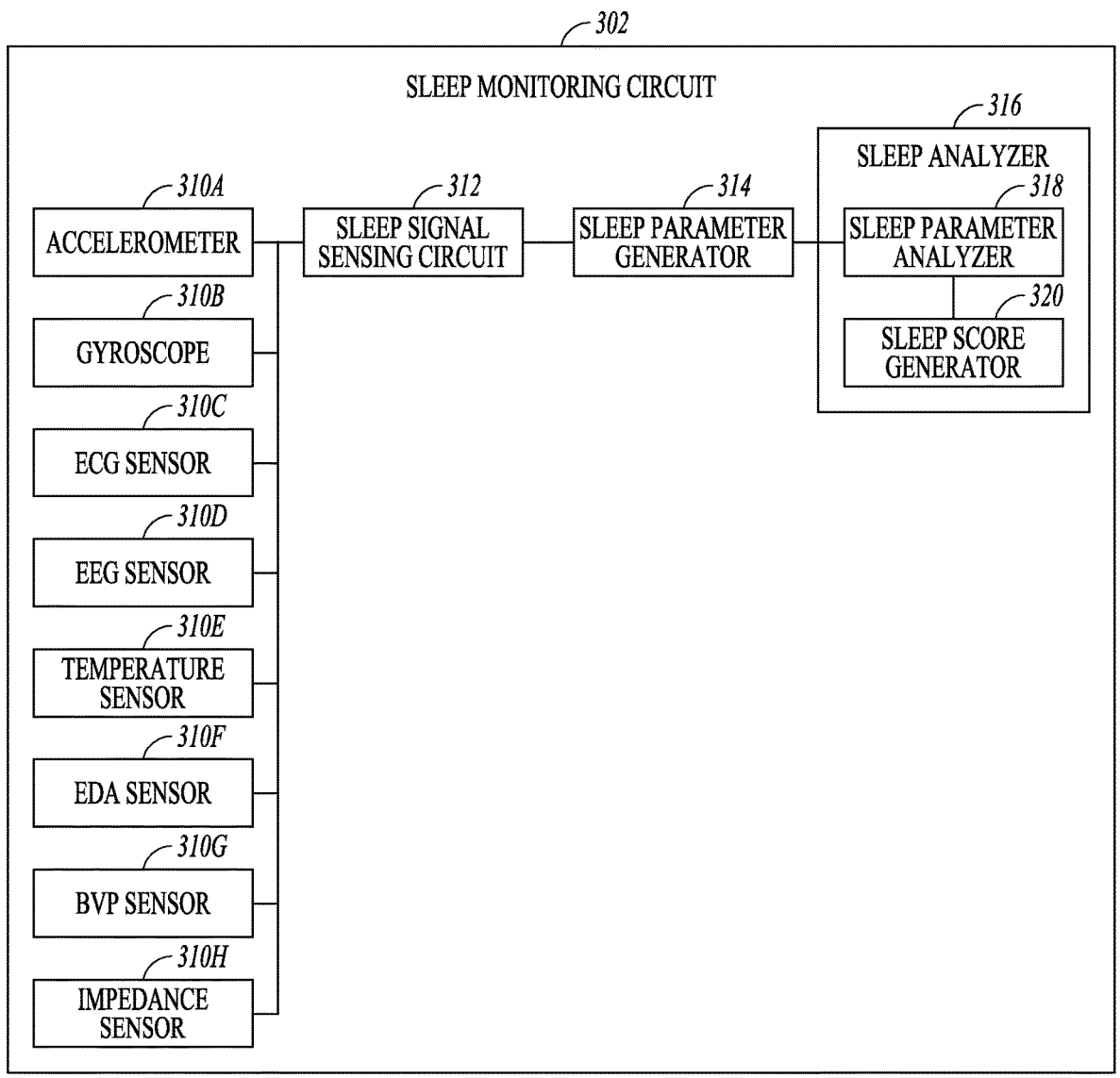
FIG. 3 illustrates another embodiment of a sleep monitoring circuit, such as may be used in the therapy system of FIG. 1.

FIG. 3 illustrates another embodiment of a sleep monitoring circuit 302, which represents an example of sleep monitoring circuit 202. Sleep monitoring circuit 302 can include one or more sleep sensors 310, a sleep signal sensing circuit 312, a sleep parameter generator (or sleep parameter generator circuit) 314, and a sleep analyzer (or sleep analyzer circuit) 316.

Sleep sensor(s) 310 can sense the one or more sleep signals. In the illustrated embodiment, sleep sensor(s) 310 includes an accelerometer 310A, a gyroscope 310B, an electrocardiogram (ECG) sensor 310C, an electroencephalogram (EEG) sensor 310D, a temperature sensor 310E, an electrodermal activity (EDA) sensor 310F, a blood volume pulse (BVP) sensor 310G, and an impedance sensor 310H. In various embodiments, sleep sensor(s) 310 can include any one or any combination of accelerometer 310A, gyroscope 310B, ECG sensor 310C, EEG sensor 310D, temperature sensor 310E, EDA sensor 310F, BVP sensor 310G, and impedance sensor 310H.

Accelerometer 310A can include a three-axis accelerometer to sense an accelerometer signal. In various embodiment, accelerometer 310A can be an externally wearable device or an implantable device. In this document, a sensor being an externally wearable device include a stand-alone externally wearable sensor or a sensor being part of an externally wearable device that performs another one or more functions; a sensor being an implantable device include a stand-alone implantable sensor or a sensor being part of an implantable device that performs another one or more functions. An externally wearable device includes a device configured to be worn on the patient but not to be implanted in the patient.

Gyroscope 310B can be a three-axis gyroscope to sense a gyroscope signal. In various embodiments, gyroscope 310B can be an externally wearable device or an implantable device.

ECG sensor 310C can include electrodes for sensing an ECG signal. In various embodiments, the ECG signal can include a surface ECG signal, a subcutaneous ECG signal, an epicardial electrogram signal, and/or an endocardial electrogram signal. ECG sensor 310C can be an externally wearable device, part of therapy-delivering device (e.g., a cardiac pacemaker), or an injectable monitoring device.

EEG sensor 310D can include electrodes for sensing an EEG signal. In various embodiments, EEG sensor 310D can be an externally wearable device (e.g., incorporated into a head cap, one or more ear plugs, or a head band), a subdermally implantable device, or incorporated into an implantable lead in the brain or on a neural target.

Temperature sensor 310E can sense a temperature signal. In various embodiments, temperature sensor 310E can be an externally wearable device to measure skin temperature, a subdermally implantable device to measure peripheral body temperature, or an implantable device to measure core body temperature.

EDA sensor 310F can sense an EDA signal. In various embodiments, EDA sensor 310F can be a device with surface electrode to measure skin conductance, such as from a hand (palmar surface), a foot (plantar surface), or a wrist (incorporated into a wrist worn monitoring device) or an implantable device that is communicatively coupled to a conductive layer (tattoo) on the skin.

BVP sensor 310G can sense a BVP signal. In various embodiments, EDA sensor 310F can be an externally wearable photoplethysmography (PPG) sensor or an implantable device to be positioned adjacent to an artery and capable of detecting pulsatile information from the artery to compute the BVP signal. Examples of that artery include common iliac artery, internal iliac artery, gonadal artery, inferior mesenteric artery, inferior rectal artery, inferior gluteal artery, superior gluteal artery, renal artery, and femoral artery. Examples of BVP sensor 310G as an implantable device can include a photoplethysmography (PPG) sensor to detect the pulsatile information (including timing, shape, and morphology) by passing light through the artery, an electrical bioimpedance or impedance cardiography sensor to detect the pulsatile information (including timing, shape, and morphology) by measuring change in impedance across artery as blood flow changes, an accelerometer to detect the pulsatile information (including timing, shape, and morphology) by measuring changes in position as shape of the artery changes during blood flow, a pressure sensor to be positioned around the artery to detect the pulsatile information the pulsatile information (including timing, shape, and morphology) by directly measuring pressure from the artery, and a pressure sensor to be positioned inside the artery to detect the pulsatile information (including timing, shape, and morphology) by directly measuring pressure within the artery. In various embodiments, BVP sensor 310G can include any one or any combination of these examples.

Impedance sensor 310H can sense a bioelectric impedance. In various embodiments, impedance sensor 310H can be an externally wearable device to measure skin impedance (e.g., allowing for measurement of heart rate) or an implantable device (e.g., allowing for measurement of respiration rate).

Sleep signal sensing circuit 312 can process the one or more sleep signals sensed by sleep sensor(s) 310, such as by filtering and/or amplifying each sensed sleep signal. Sleep parameter generator 314 can generate one or more sleep parameters corresponding to the sleep state of the patient using the processed one or more sleep signals. The structure and functional capability of sleep signal sensing circuit 312 and sleep parameter generator 314 depend on which sleep sensor(s) are included in sleep sensor(s) 310. In various embodiments, the one or more sleep parameters have one or more values, when used individually or in combination, that can indicate the patient's sleep state.

Sleep analyzer 316 represents an example of sleep analyzer 216 and can determine the sleep state of the patient using the one or more sleep parameters generated by sleep parameter generator 314. Sleep analyzer 316 analyzer 316 can include a sleep parameter analyzer (or sleep parameter analyzer circuit) 318 and a sleep score generator (or sleep score generator circuit) 320. Sleep parameter analyzer 318 can receive and analyze the one or more sleep parameters. In one embodiment, the one or more sleep parameters have values indicative of the patient's sleep stages. For example, the values of the one or more sleep parameters can be mapped to the sleep stages using data collected from the patient or collected from a patient population. Sleep stage can be classified as, but not being limited to, awake, slow-wave sleep, REM sleep, non-REM1 sleep, or non-REM2. Analysis of the one or more sleep parameters can result in the current sleep stage of the patient as well as time and/or percentage of time spent in each sleep stage. Sleep score generator 320 can compute a sleep score indicative of sleep stage or quality using an outcome of the analysis of the one or more sleep parameters. For example, value ranges each corresponding to one of sleep stages may be determined for each of the one or more sleep parameters for the patient, and used for computing the sleep score as a function of the sleep stage. In various embodiments, the sleep score can include a number (numerical value), a sleep signal metric, and/or a number being a function of the sleep signal metric.

In one embodiment, sleep parameter analyzer 318 produces a sleep signal metric using the one or more sleep parameters. The sleep signal metric can be a linear or nonlinear combination of multiple sleep parameters. In one embodiment, sleep parameter analyzer 318 produces the sleep signal metric using the multiple sleep parameters with the weighting factors each applied to one of these parameters. In one embodiment, sleep parameter analyzer 318 adjusts the weighting factors through automatic learning and adaptation to the patient over time (e.g., based on stored parameters and/or outcomes of analysis, such as features extracted from the parameters). In another embodiment, sleep parameter analyzer 318 allows the weighting factors to be adjusted manually. In one embodiment, the weighting factors are adjusted according to a calibration schedule or as needed, and the adjustment can be performed by a user such as a physician or other authorized care provider in a clinic, or initiated by the patient and performed by the sleep parameter analyzer automatically at home. In one embodiment, the weighting factors can be patient-specific and dynamically changed based on the patient's conditions and/or activities, such as the pathological condition(s) for which the patient is treated, physical condition, time of day, and/or physical activity. In one embodiment, sleep score generator 320 computes the sleep score using the sleep signal metric.

In one embodiment, pain score generator 320 trends the sleep signal metric and computes the sleep score using the resulting trending of the sleep signal metric.

Figure 4:
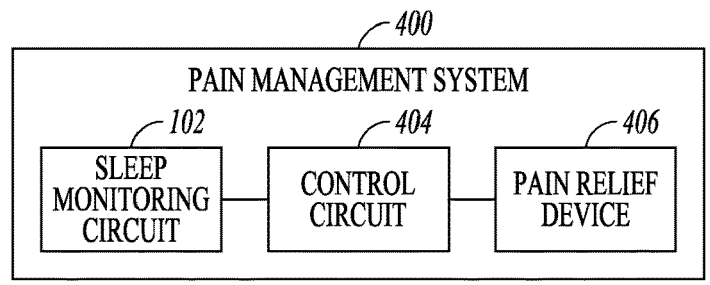
FIG. 4 illustrates an embodiment of a pain management system.

FIG. 4 illustrates an embodiment of a pain management system 400, which represent an example of therapy system 100. Pain management system 400 can include sleep monitoring circuit 102 (including its various embodiments as discussed for sleep monitoring circuit 202 and 302), a control circuit 404, and a pain relief device 406.

Pain relief device 406 can deliver one or more pain relief therapies for treating chronic pain and/or symptoms associated with the chronic pain. In various embodiments, pain relief device 406 can include a neurostimulator (also referred to as neuromodulator) to deliver neurostimulation (also referred to as neuromodulation) to neural tissue such as the spinal cord, brain, and peripheral nerves or a drug pump to delivery drug into the body locally, such as in the intrathecal space. In one embodiment, the neurostimulator includes a pulse generator to generate and deliver electrical stimulation pulses. In other embodiments, the neurostimulator can deliver neurostimulation that uses any form of stimulation energy or agent as stimuli that is capable of modulating neural activities and/or properties.

In various embodiments, pain relief device 406 can deliver any one or any combination of spinal cord stimulation (SCS), dorsal root ganglia (DRG) stimulation, deep brain stimulation (DBS), motor cortex stimulation (MCS), transcranial direct current stimulation (tDCS), transcutaneous spinal direct current stimulation (tsDCS), trigeminal nerve stimulation, occipital nerve stimulation, vagus nerve stimulation (VNS), sacral nerve stimulation, pudendal nerve stimulation, sphenopalatine ganglion stimulation, sympathetic nerve modulation, multifidus muscle stimulation, adrenal gland modulation, carotid baroreceptor stimulation, transcutaneous electrical nerve stimulation (TENS), transcranial magnetic stimulation (TMS), tibial nerve stimulation, transcranial magnetic stimulation (TMS), radiofrequency ablation (RFA), pulsed radiofrequency ablation, ultrasound therapy, high-intensity focused ultrasound (HIFU), optical stimulation, optogenetic therapy, magnetic stimulation, other peripheral tissue stimulation therapies, other peripheral tissue denervation therapies, drug therapy (such as delivered from a drug pump), and nerve blocks or injections (such as pharmaceuticals or biologics).

Control circuit 404 can control the delivery of the one or more pain relief therapies using therapy parameters and can adjust the therapy parameters based on the sleep state, such as indicated by the pain score or pain signal metric, such that the delivery of the one or more pain relief therapies is adjusted in a way reflecting changes in the sleep state. When pain relief device 406 delivers the neurostimulation, control circuit 404 can control the delivery of the neurostimulation using stimulation parameters and can adjust the stimulation parameters based on the sleep state. In various embodiments, control circuit 404 can optimize the stimulation parameters for the determined sleep state. In various embodiments, control circuit 404 can execute a closed-loop neurostimulation algorithm for treating chronic pain or a disorder related to the chronic pain using the determined sleep state as an input.

Figure 5:
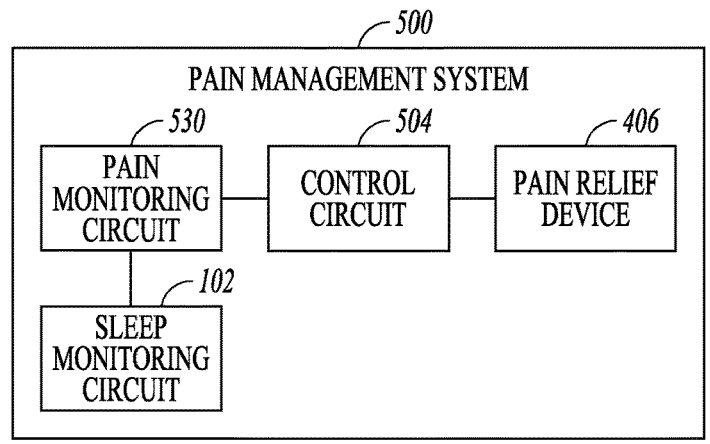
FIG. 5 illustrates another embodiment of pain management system.

FIG. 5 illustrates an embodiment of pain management system 500, which represent another example of therapy system 100. Pain management system 500 can include sleep monitoring circuit 102 (including its various embodiments as discussed for sleep monitoring circuit 202 and 302), a pain monitoring circuit 530, a control circuit 504, and pain relief device 406.

Pain monitoring circuit 530 can sense one or more pain signals from the patient and produce a measure of pain of the patient using the one or more pain-related physiological signals. The one or more pain signals can include one or more physiological signals corresponding to the pain of the patient. In one embodiment, the measure of pain includes a pain score quantitatively indicative of a degree of the pain.

Control circuit 504 can control the delivery of the one or more pain relief therapies from pain relief device 406 using therapy parameters and can adjust the therapy parameters based on the sleep state determined by sleep monitoring circuit 102 and the measure of the pain produced by pain monitoring circuit 530. In one embodiment, control circuit 504 can adjust the therapy parameters based on the sleep score and the pain score. This can be achieved by, for example, producing the pain score using the sleep score as an input, and adjusting the therapy parameters using the pain score. In one embodiment, control circuit 504 can control the delivery of the one or more pain relief therapies using the therapy parameters and can adjust the therapy parameters using the pain score (which is a function of the sleep score). In one embodiment, control circuit 504 can optimize the stimulation parameters for the determined sleep state. In various embodiments, control circuit 504 can execute a closed-loop therapy algorithm for treating chronic pain or a disorder related to the chronic pain using the pain score (which is a function of the sleep score) as an input.

Figure 6:
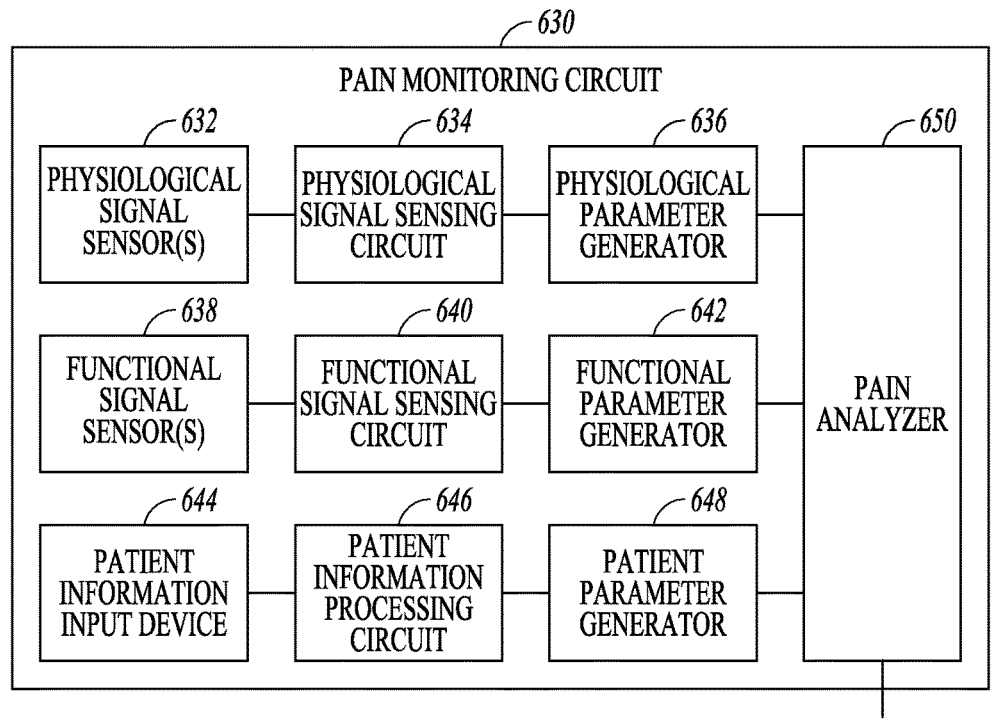
FIG. 6 illustrates an embodiment of a pain monitoring circuit, such as may be used in the therapy system of FIG. 5.

FIG. 6 illustrates an embodiment of a pain monitoring circuit 630, which represents an example of pain management circuit 530. In the illustrated embodiment, pain monitoring circuit 630 can determine the measure of pain, such as the pain score, using the sleep state, such as the sleep score, as discussed in this document, as well as one or more physiological parameters each indicative of a physiological function or physiological state of a patient that is related to pain, one or more functional parameters each indicative of a physical activity or physical state of the patient that is related to pain, and one or more patient parameters related to the pain, such as a parameter representative of intensity of the pain specified by the patient. In various embodiments, pain monitoring circuit 630 can determine the pain score using the sleep score and at least one of a physiological parameter, a functional parameter, or a patient parameter. In some embodiments, pain monitoring circuit 630 can determine the pain score using the sleep score and at least a physiological parameter and a functional parameter.

In the illustrated embodiment, pain monitoring circuit 630 includes one or more physiological signal sensors 632, a physiological signal sensing circuit 634, a physiological parameter generator (or physiological parameter generator circuit) 636, one or more functional signal sensors 638, a functional signal sensing circuit 640, a functional parameter generator (or functional parameter generator circuit) 642, a patient information input device 644, a patient information processing circuit 646, a patient parameter generator (or patient parameter generator circuit) 648, and a pain analyzer (or pain analyzer circuit) 650. In various embodiments, pain monitoring circuit 630 can include at least one or more physiological signal sensors 632, physiological signal sensing circuit 634, physiological parameter generator 636, one or more functional signal sensors 638, functional signal sensing circuit 640, functional parameter generator 642, and pain analyzer 650.

In various embodiments, one or more physiological signal sensors 632 can each sense one or more physiological signals, and can each be a non-invasive, percutaneous, or implantable sensor. Physiological signal sensing circuit 634 can process the one or more physiological signals. Physiological parameter generator 636 can generate the one or more physiological parameters using the processed one or more physiological signals. In various embodiments, one or more functional signal sensors 638 can sense one or more functional signals, and can each be a non-invasive, percutaneous, or implantable sensor. Functional signal sensing circuit 640 can process the one or more functional signals. Functional parameter generator 642 can generate the one or more functional parameters using the processed one or more functional signals. In various embodiments, patient information input device 644 can receive patient information related to pain. Patient information processing circuit 646 can process the patient information. Patient parameter generator 648 can generate one or more patient parameters using the processed patient information. Examples of the one or more physiological parameters, the one or more functional parameters, and the one or more patient parameters are discussed in U.S. Provisional Patent Application Ser. No. 62/400,336, entitled "METHOD AND APPARATUS FOR PAIN MANAGEMENT USING OBJECTIVE PAIN MEASURE", filed on Sep. 27, 2016, assigned to Boston Scientific Neuromodulation Corporation, which is incorporated herein by reference in its entirety.

Pain analyzer 630 can receive the one or more physiological parameters from physiological parameter generator 636, the one or more functional parameters from functional parameter generator 642, and/or the one or more patient parameters from patient parameter generator 648, and also receive the sleep score from sleep monitoring circuit 102. Pain analyzer 630 can analyze the received parameters including the sleep score and computes the pain score using an outcome of the analysis. The pain score indicates a degree of the pain. In one embodiment, pain analyzer 650 produces a signal metric using the received parameters, and computes the composite pain score using the signal metric. In one embodiment, pain analyzer 650 trends the signal metric and computes the composite pain score based on the resulting trending of the signal metric. The signal metric can be a linear or nonlinear combination of the sleep score and the one or more physiological parameters, the one or more functional parameters, and/or the one or more patient parameters. In one embodiment, pan analyzer 650 produces the signal metric using the received parameters with the weighting factors each applied to one of these parameters. In various embodiments, pan analyzer 650 adjusts the weighting factors through automatic learning and adaptation to the patient over time, and/or allows the weighting factors to be adjusted manually. In one embodiment, the weighting factors can be adjusted according to a calibration schedule or as needed, and the adjustment can be performed by the user. In various embodiments, the weighting factors can be patient-specific and dynamically changed based on the patient's conditions and/or activities.

Figure 7:
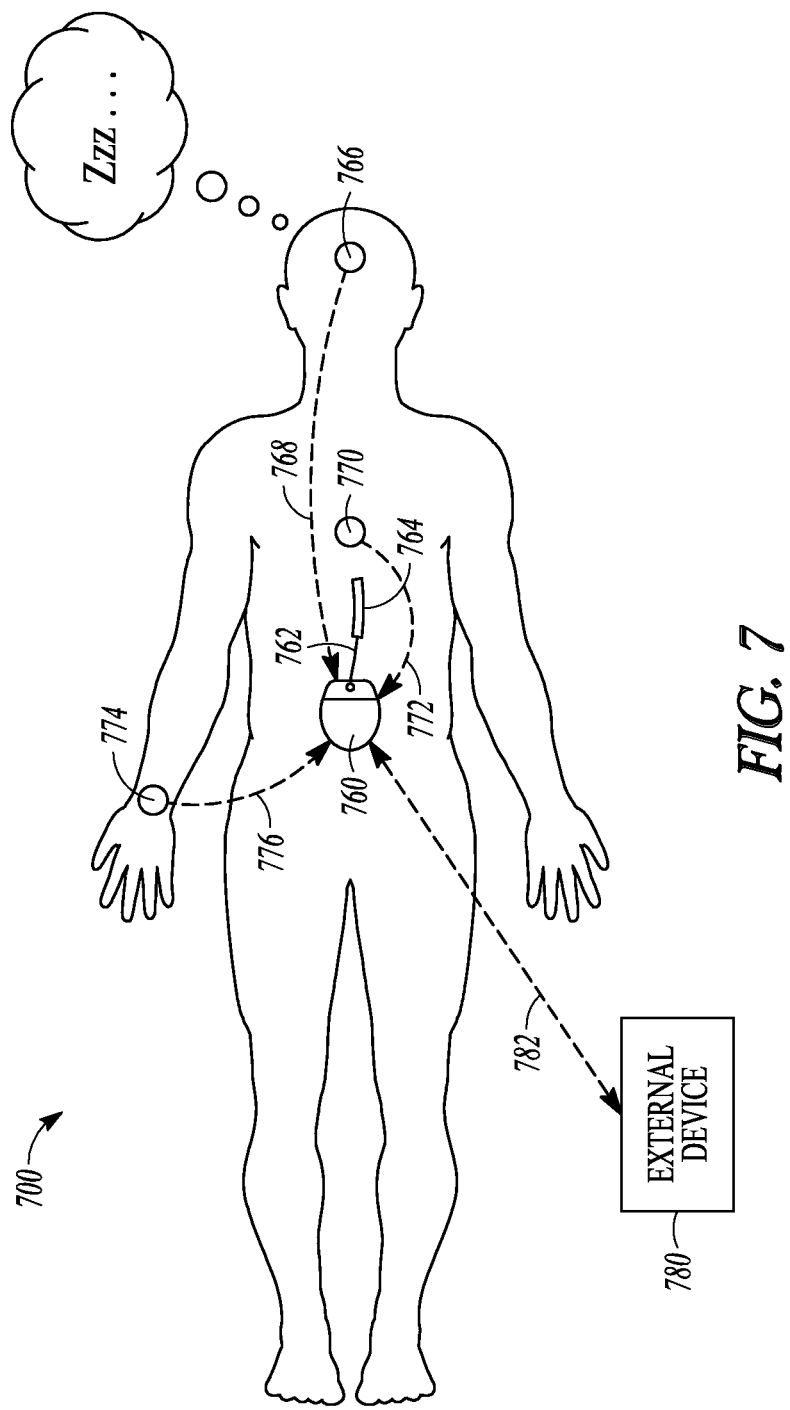
FIG. 7 illustrates an embodiment of a pain management system, such as one in which the pain management system of FIG. 4 or 5 may be implemented, and portions of an environment in which the pain management system may be used.

FIG. 7 illustrates an embodiment of a pain management system 700, such as one in which pain management system 400 or 500 may be implemented, and portions of an environment in which pain management system 700 may be used. Pain management system 700 can include an implantable medical device 760, an implantable lead or lead system 762 connected to implantable medical device 760, an external device 780 communicatively coupled to implantable medical device 760 via a wireless communication link 782, a sensor 766 communicatively coupled to implantable medical device 760 via a wireless communication link 768, a sensor 770 communicatively coupled to implantable medical device 760 via a wireless communication link 772, and sensor 774 communicatively coupled to implantable medical device 760 via a wireless communication link 776. A pain monitoring circuit such as pain monitoring circuit 530 or 630 can be contained within implantable medical device 760 or distributed in implantable medical device 760 and external device 780. Implantable medical device 760 can include a therapy device such as pain relief device 406 to deliver one or more pain relief therapies. In various embodiments, external device 780 can be implemented as a dedicated device or in a generic device such as a smartphone, a laptop computer, or a tablet computer.

In the illustrated embodiment, lead or lead system 762 includes an electrode or electrode array 764. In various embodiments, additional one or more electrodes can be incorporated onto implantable medical device 760. In the illustrated embodiment, sensor 766 can include an EEG sensor such as EEG sensor 310D, sensor 770 can include an ECG sensor such as ECG sensor 310C, and sensor 774 can include an EDA sensor such as EDA sensor 310F. Sensors 766, 770, and 774 can each be an implantable sensor or an externally wearable sensor. In various embodiments, the sleep score and the pain score can be produced by implantable medical device 760 using signals sensed by sensors 766, 770, and 774.

The sizes and shapes of the elements of pain management system 700 and their locations relative to the patient's body are illustrated by way of example and not by way of restriction. Pain management system 700 is discussed as a specific application of pain management according to various embodiments of the present subject matter. In various embodiments, the present subject matter may be applied in any type of pain management in controlling delivery of one or more pain relief energy and/or agents from an implantable or externally wearable medical device.

Figure 8:
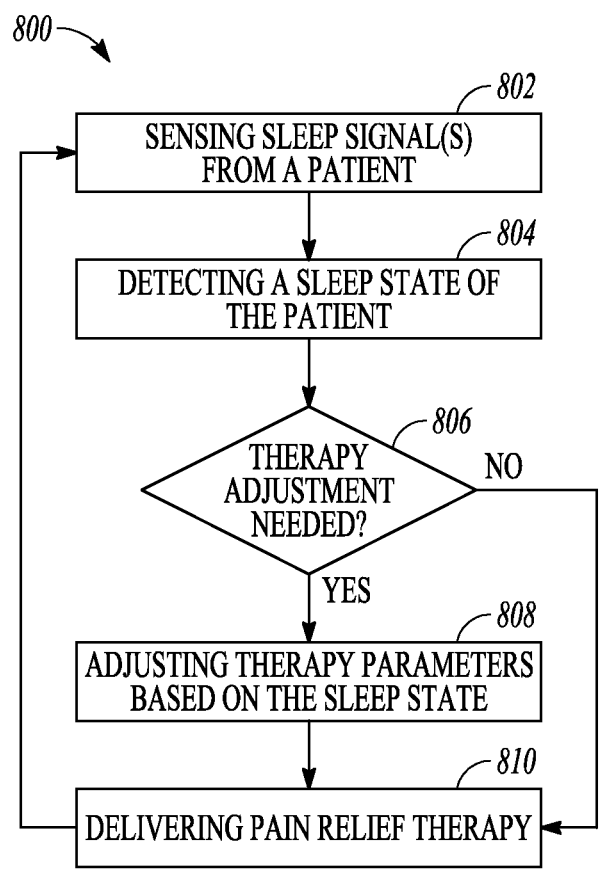
FIG. 8 illustrates an embodiment of a method for pain management.

FIG. 8 illustrates an embodiment of a method 800 for pain management. In various embodiments, pain management system 400, 500, or 700 can be configured to perform method 800.

At 802, one or more sleep signals are sensed from the patient. The one or more sleep signals can include one or more physiological signals corresponding to the sleep state of the patient. In various embodiments, the one or more sleep signals can each be sensed using a sensor implanted in the patient or a sensor externally worn by the patient. In various embodiments, the one or more sleep signals can each be sensed using a sensor incorporated into a medical device that delivers a pain relief therapy or a sensor communicatively coupled to the medical device via a wireless link. Examples for the one or more sleep signals include an accelerometer signal, a gyroscope signal, an electrocardiogram (ECG) signal, an electroencephalogram (EEG) signal, a temperature signal of the one or more sleep signals, an electrodermal activity (EDA) signal, and a blood volume pulse (BVP) signal, as discussed with reference to FIG. 3.

At 804, a sleep state of the patient is determined using the one or more sleep signals. In one embodiment, the sleep state can be awake or a sleep stage identified from predefined sleep stages. There are different ways to define sleep stages. In one example, the sleep stages include non-REM sleep stages 1-4 and REM sleep. In another example, the sleep stages include non-REM sleep stages 1-3 and REM sleep. In yet another example, the sleep stages include slow-wave sleep, REM sleep, non-REM1 sleep, or non-REM2. The present subject matter applies regardless of how sleep stages are defined. In various embodiments, a sleep score representing the sleep state is produced using the one or more sleep signals. The sleep score can indicate the sleep stage, and can include a number, a sleep signal metric, or a number being a function of the sleep signal metric. In various embodiments, in addition to the steep state (e.g., the sleep score), one or more physiological parameters each indicative of a physiological function or physiological state of the patient, one or more functional parameters each indicative of a physical activity or physical state of the patient, and/or one or more patient parameters each including subjective information provided by the patient are received and analyzed to compute a pain score. The pain score can indicate a degree of the pain of the patient.

At 806, whether the sleep score and/or the pain score indicate a need for therapy adjustment is determined. If the sleep score and/or the pain score indicate a need for the therapy adjustment, one or more therapy parameters are adjusted using the sleep score and/or the pain score at 808, and a pain relief therapy is delivered as controlled using a plurality of therapy parameters including the adjusted one or more therapy parameters at 810. If the sleep score and/or the pain score do not indicate a need for the therapy adjustment, the pain relief therapy is delivered at 810 without adjusting the one or more therapy parameters. In one embodiment, only the pain score is directly used to indicate the need for therapy adjustment because the pain score is determined as a function of the sleep score. Examples of the pain relief therapy include those deliverable from pain relief device 406, as discussed with reference to FIG. 4.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for delivering neurostimulation to a patient, the method comprising:
   sensing one or more sleep signals and one or more pain signals from the patient, the one or more sleep signals including one or more physiological signals corresponding to sleep stages of the patient, the one or more pain signals indicative of pain of the patient;
   determining the sleep stages of the patient using the one or more sleep signals;
   determining a measure associated with the pain of the patient using the one or more pain signals and each sleep stage of the determined sleep stages;
   controlling delivery of neurostimulation using stimulation parameters;
   adjusting the stimulation parameters using the determined measure associated with the pain of the patient for controlling the delivery of the neurostimulation during the each sleep stage of the determined sleep stages; and
   delivering the neurostimulation.

2. The method of claim 1, wherein determining the sleep stages comprises producing sleep scores using the one or more sleep signals, the sleep scores each indicative of a stage of the sleep stages and including one or more of a number, a sleep signal metric, or a number being a function of the sleep signal metric, and determining the measure associated with the pain of the patient using the one or more pain signals and each stage of the determined sleep stages comprises determining a pain score using the one or more pain signals and the sleep score indicative of the each stage.

3. The method of claim 1, wherein sensing the one or more sleep signals from the patient comprises sensing at least one of an accelerometer signal, a gyroscope signal, an electrocardiogram (ECG) signal, an electroencephalogram (EEG) signal, a temperature signal of the one or more sleep signals, an electrodermal activity (EDA) signal, a blood volume pulse (BVP) signal, or a bioelectric impedance signal.

4. The method of claim 1, wherein delivering the neurostimulation comprises delivering the neurostimulation from a medical device implanted in the patient or externally worn by the patient.

5. The method of claim 4, wherein sensing the one or more sleep signals comprises sensing at least one sleep signal of the one or more sleep signals using a sensor implanted in the patient.

6. The method of claim 4, wherein sensing the one or more sleep signals comprises sensing at least one sleep signal of the one or more sleep signals using a sensor externally worn by the patient.

7. The method of claim 4, wherein sensing the one or more sleep signals comprises sensing at least one sleep signal of the one or more sleep signals using a sensor communicatively coupled to the medical device via a wireless link.

8. The method of claim 1, wherein delivering the neurostimulation comprises delivering the neurostimulation from a medical device implanted in the patient, and sensing the one or more sleep signals comprises sensing at least one sleep signal of the one or more sleep signals using a sensor externally worn by the patient.

9. The method of claim 8, wherein sensing the one or more sleep signals comprises sensing an electrocardiogram (ECG) signal.

10. The method of claim 8, wherein sensing the one or more sleep signals comprises sensing an electroencephalogram (EEG) signal.

11. The method of claim 1, wherein adjusting the stimulation parameters comprises optimizing the stimulation parameters for each sleep stage of the determined sleep stages.

12. A method for delivering neurostimulation to a patient, the method comprising:
    delivering a pain relief therapy including the neurostimulation to the patient;
    sensing one or more sleep signals indicative of sleeping stages of the patient;
    determining the sleep stages of the patient using the one or more sleep signals;
    sensing one or more pain signals indicative of pain of the patient;
    determining a pain score using the one or more pain signals and each sleep stage of the determined sleep stages, the pain score indicative of a degree of the pain of the patient;
    determining stimulation parameters for each sleep stage of the determined sleep stages using the determined pain score; and
    controlling the delivery of the neurostimulation during each sleep stage of the determined sleep stages using stimulation parameters determined for that sleep stage.

13. The method of claim 12, wherein sensing the one or more sleep signals comprises sensing an electrocardiogram (ECG) signal.

14. The method of claim 12, wherein sensing the one or more sleep signals comprises sensing an electroencephalogram (EEG) signal.

15. The method of claim 12, wherein sensing the one or more sleep signals comprises sensing at least one sleep signal of the one or more sleep signals using an external medical device configured to be worn by the patient.

16. The method of claim 15, wherein delivering the neurostimulation to the patient comprises delivering the neurostimulation from a neurostimulator implanted in the patient.

17. The method of claim 15, wherein sensing the one or more sleep signals comprises sensing at least one of an accelerometer signal, a gyroscope signal, an electrocardiogram (ECG) signal, an electroencephalogram (EEG) signal, a temperature signal of the one or more sleep signals, an electrodermal activity (EDA) signal, a blood volume pulse (BVP) signal, or a bioelectric impedance signal.

18. The method of claim 15, wherein delivering the neurostimulation to the patient comprises delivering the neurostimulation from a neurostimulator externally worn by the patient.

19. The method of claim 12, wherein controlling the delivery of the neurostimulation comprises executing a closed-loop neurostimulation algorithm for treating chronic pain or a disorder related to the chronic pain using the determined sleep stages as an input.

20. The method of claim 12, wherein determining the stimulation parameters for each sleep stage of the determined sleep stages comprises optimizing the stimulation parameters for the each stage.

* * * * *